Figure 1:
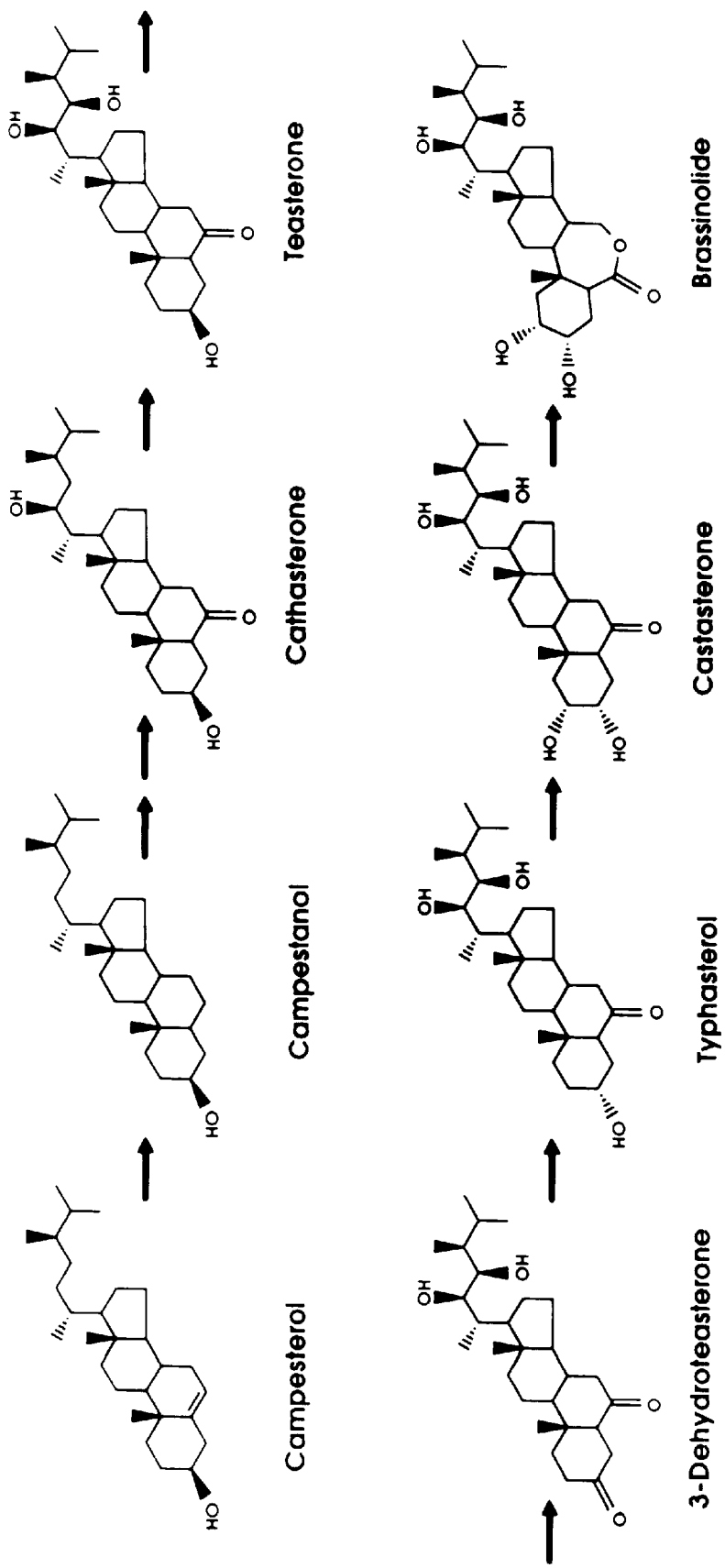

United States Patent [19]
Koncz et al.

[11] Patent Number: 5,952,545
[45] Date of Patent: Sep. 14, 1999

[54] NUCLEIC ACID MOLECULES ENCODING CYTOCHROME P450-TYPE PROTEINS INVOLVED IN THE BRASSINOSTEROID SYNTHESIS IN PLANTS

[75] Inventors: Csaba Koncz; Jaideep Mathur, both of Köln; Miklos Szekeres, Szeged; Thomas Altmann, Berlin, all of Germany

[73] Assignee: Max-Planck-Gesellschaft zur Forderung der Wissenschaften e.V., Berlin, Germany

[21] Appl. No.: 08/622,166

[22] Filed: Mar. 27, 1996

[51] Int. Cl.⁶ .......................... C12N 15/29; C12N 15/82; C12N 15/00; A01H 4/00
[52] U.S. Cl. .......................... 800/298; 800/295; 800/278; 435/69.1; 435/468; 435/419; 435/320.1; 536/24.1; 536/23.6
[58] Field of Search .................................. 800/205, 295, 800/298, 278; 435/69.1, 172.3, 320.1, 419; 536/24.1, 23.6

[56] References Cited

PUBLICATIONS

Napoli et al. The Plant Cell. vol. 2, Apr. 1990, pp. 279–289.

Primary Examiner—Lynette F. Smith
Assistant Examiner—Thomas Haas
Attorney, Agent, or Firm—Birch, Stewart, Kolasch & Birch, LLP

[57] ABSTRACT

The invention describes nucleic acid molecules encoding cytochrome P450-type proteins involved in the brassionosteroid synthesis in plants, transgenic plant cells and plants containing such nucleic acid molecules as well as processes for the identification of other proteins involved in brassinosteroid synthesis and processes for the identification of substances acting as brassinosteroids or as brassinosteroid inhibitors in plants.

22 Claims, 12 Drawing Sheets

Fig. 6A

Fig. 6B

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1608 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: A. thaliana (vii) IMMEDIATE SOURCE:
      (A) LIBRARY: lambda gt10
      (B) CLONE: C204

(ix) FEATURE:
      (A) NAME/KEY: CDS
      (B) LOCATION:48..1466

(xi) SEQUENCE DESCRIPTION: SEQ ID NO: 1:

```
TCTCTCCCTC ATCCTCTCTT CTTCTCTCAT CATCATCTTC TTCTTCA ATG GCC TTC        56
                                                   Met Ala Phe
                                                     1

ACC GCT TTT CTC CTC CTC CTC TCT TCC ATC GCC GCC GGC TTC CTC CTC       104
Thr Ala Phe Leu Leu Leu Leu Ser Ser Ile Ala Ala Gly Phe Leu Leu
      5                  10                  15

CTA CTC CGC CGT ACA CGT TAC CGT CGG ATG GGT CTG CCT CCG GGA AGC       152
Leu Leu Arg Arg Thr Arg Tyr Arg Arg Met Gly Leu Pro Pro Gly Ser
 20                  25                  30                  35

CTT GGT CTC CCT CTG ATA GGA GAG ACT TTT CAG CTG ATC GGA GCT TAC       200
Leu Gly Leu Pro Leu Ile Gly Glu Thr Phe Gln Leu Ile Gly Ala Tyr
                 40                  45                  50

AAA ACA GAG AAC CCT GAG CCT TTC ATC GAC GAG AGA GTA GCC CGG TAC       248
Lys Thr Glu Asn Pro Glu Pro Phe Ile Asp Glu Arg Val Ala Arg Tyr
             55                  60                  65

GGT TCG GTT TTC ATG ACG CAT CTT TTT GGT GAA CCG ACG ATT TTC TCA       296
Gly Ser Val Phe Met Thr His Leu Phe Gly Glu Pro Thr Ile Phe Ser
         70                  75                  80

GCT GAC CCG GAA ACG AAC CGG TTT GTT CTT CAG AAC GAA GGG AAG CTT       344
Ala Asp Pro Glu Thr Asn Arg Phe Val Leu Gln Asn Glu Gly Lys Leu
     85                  90                  95

TTT GAG TGT TCT TAT CCT GCT TCC ATT TGT AAC CTT TTG GGG AAA CAC       392
Phe Glu Cys Ser Tyr Pro Ala Ser Ile Cys Asn Leu Leu Gly Lys His
100                 105                 110                 115

TCT CTG CTT CTT ATG AAA GGT TCT TTG CAT AAA CGT ATG CAC TCT CTC       440
Ser Leu Leu Leu Met Lys Gly Ser Leu His Lys Arg Met His Ser Leu
                120                 125                 130

ACC ATG AGC TTT GCT AAT TCT TCA ATC ATT AAA GAC CAT CTC ATG CTT       488
Thr Met Ser Phe Ala Asn Ser Ser Ile Ile Lys Asp His Leu Met Leu
            135                 140                 145

GAT ATT GAC CGG TTA GTC CGG TTT AAT CTT GAT TCT TGG TCT TCT CGT       536
Asp Ile Asp Arg Leu Val Arg Phe Asn Leu Asp Ser Trp Ser Ser Arg
        150                 155                 160

GTT CTC CTC ATG GAA GAA GCC AAA AAG ATA ACG TTT GAG CTA ACG GTG       584
```

-continued

| | | |
|---|---|---|
| Val Leu Leu Met Glu Glu Ala Lys Lys Ile Thr Phe Glu Leu Thr Val<br>165 170 175 | | |
| AAG CAG TTG ATG AGC TTT GAT CCA GGG GAA TGG AGT GAG AGT TTA AGG<br>Lys Gln Leu Met Ser Phe Asp Pro Gly Glu Trp Ser Glu Ser Leu Arg<br>180 185 190 195 | 632 | |
| AAA GAG TAT CTT CTT GTC ATC GAA GGC TTC TTC TCT CTT CCT CTC CCT<br>Lys Glu Tyr Leu Leu Val Ile Glu Gly Phe Phe Ser Leu Pro Leu Pro<br>200 205 210 | 680 | |
| CTC TTC TCC ACC ACT TAC CGC AAA GCC ATC CAA GCG CGG AGG AAG GTG<br>Leu Phe Ser Thr Thr Tyr Arg Lys Ala Ile Gln Ala Arg Arg Lys Val<br>215 220 225 | 728 | |
| GCG GAG GCG TTG ACG GTG GTG GTG ATG AAA AGG AGG GAG GAG GAG GAA<br>Ala Glu Ala Leu Thr Val Val Val Met Lys Arg Arg Glu Glu Glu Glu<br>230 235 240 | 776 | |
| GAA GGA GCG GAG AGA AAG AAA GAT ATG CTT GCG GCG TTG CTT GCG GCG<br>Glu Gly Ala Glu Arg Lys Lys Asp Met Leu Ala Ala Leu Leu Ala Ala<br>245 250 255 | 824 | |
| GAT GAT GGA TTT TCC GAT GAA GAG ATT GTT GAC TTC TTG GTG GCT TTA<br>Asp Asp Gly Phe Ser Asp Glu Glu Ile Val Asp Phe Leu Val Ala Leu<br>260 265 270 275 | 872 | |
| CTT GTC GCC GGT TAT GAA ACA ACC TCC ACG ATC ATG ACT CTC GCC GTC<br>Leu Val Ala Gly Tyr Glu Thr Thr Ser Thr Ile Met Thr Leu Ala Val<br>280 285 290 | 920 | |
| AAA TTT CTC ACC GAG ACT CCT TTA GCT CTT GCT CAA CTC AAG GAA GAG<br>Lys Phe Leu Thr Glu Thr Pro Leu Ala Leu Ala Gln Leu Lys Glu Glu<br>295 300 305 | 968 | |
| CAT GAA AAG ATT AGG GCA ATG AAG AGT GAT TCG TAT AGT CTT GAA TGG<br>His Glu Lys Ile Arg Ala Met Lys Ser Asp Ser Tyr Ser Leu Glu Trp<br>310 315 320 | 1016 | |
| AGT GAT TAC AAG TCA ATG CCA TTC ACA CAA TGT GTG GTT AAT GAG ACG<br>Ser Asp Tyr Lys Ser Met Pro Phe Thr Gln Cys Val Val Asn Glu Thr<br>325 330 335 | 1064 | |
| CTA CGA GTG GCT AAC ATC ATC GGC GGT GTT TTC AGA CGT GCA ATG ACG<br>Leu Arg Val Ala Asn Ile Ile Gly Gly Val Phe Arg Arg Ala Met Thr<br>340 345 350 355 | 1112 | |
| GAT GTT GAG ATC AAA GGT TAT AAA ATT CCA AAA GGG TGG AAA GTA TTC<br>Asp Val Glu Ile Lys Gly Tyr Lys Ile Pro Lys Gly Trp Lys Val Phe<br>360 365 370 | 1160 | |
| TCA TCG TTT AGA GCG GTT CAT TTA GAC CCA AAC CAC TTC AAA GAT GCT<br>Ser Ser Phe Arg Ala Val His Leu Asp Pro Asn His Phe Lys Asp Ala<br>375 380 385 | 1208 | |
| CGC ACT TTC AAC CCT TGG AGA TGG CAG AGC AAC TCG GTA ACG ACA GGC<br>Arg Thr Phe Asn Pro Trp Arg Trp Gln Ser Asn Ser Val Thr Thr Gly<br>390 395 400 | 1256 | |
| CCT TCT AAT GTG TTC ACA CCG TTT GGT GGA GGG CCA AGG CTA TGT CCC<br>Pro Ser Asn Val Phe Thr Pro Phe Gly Gly Gly Pro Arg Leu Cys Pro<br>405 410 415 | 1304 | |
| GGT TAC GAG CTG GCT AGG GTT GCA CTC TCT GTT TTC CTT CAC CGC CTA<br>Gly Tyr Glu Leu Ala Arg Val Ala Leu Ser Val Phe Leu His Arg Leu<br>420 425 430 435 | 1352 | |
| GTG ACA GGC TTC AGT TGG GTT CCT GCA GAG CAA GAC AAG CTG GTT TTC<br>Val Thr Gly Phe Ser Trp Val Pro Ala Glu Gln Asp Lys Leu Val Phe<br>440 445 450 | 1400 | |
| TTT CCA ACT ACA AGA ACG CAG AAA CGG TAC CCG ATC TTC GTG AAG CGC<br>Phe Pro Thr Thr Arg Thr Gln Lys Arg Tyr Pro Ile Phe Val Lys Arg<br>455 460 465 | 1448 | |
| CGT GAT TTT GCT ACT TGA AGAAGAAGAG ACCCATCTGA TTTTATTTAT<br>Arg Asp Phe Ala Thr *<br>470 | 1496 | |
| AGAACAACAG TATTTTTCAG GATTAATTTC TTCTTCTTTT TTTGCCTCCT TGTGGGTCTA | 1556 | |

GTGTTTGACA ATAAAAGTTA TCATTACTCT ATAAAGCCTT AGCTTCTGTG TA         1608

(2) INFORMATION FOR SEQ ID NO: 2:

(i) SEQUENCE CHARACTERISTICS:
        (A) LENGTH: 472 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Phe Thr Ala Phe Leu Leu Leu Ser Ser Ile Ala Ala Gly
 1               5                  10                  15

Phe Leu Leu Leu Arg Arg Thr Arg Tyr Arg Arg Met Gly Leu Pro
             20                  25                  30

Pro Gly Ser Leu Gly Leu Pro Leu Ile Gly Glu Thr Phe Gln Leu Ile
             35                  40                  45

Gly Ala Tyr Lys Thr Glu Asn Pro Glu Pro Phe Ile Asp Glu Arg Val
        50                   55                  60

Ala Arg Tyr Gly Ser Val Phe Met Thr His Leu Phe Gly Glu Pro Thr
 65                  70                  75                  80

Ile Phe Ser Ala Asp Pro Glu Thr Asn Arg Phe Val Leu Gln Asn Glu
                 85                  90                  95

Gly Lys Leu Phe Glu Cys Ser Tyr Pro Ala Ser Ile Cys Asn Leu Leu
            100                 105                 110

Gly Lys His Ser Leu Leu Met Lys Gly Ser Leu His Lys Arg Met
            115                 120                 125

His Ser Leu Thr Met Ser Phe Ala Asn Ser Ser Ile Ile Lys Asp His
130                 135                 140

Leu Met Leu Asp Ile Asp Arg Leu Val Arg Phe Asn Leu Asp Ser Trp
145                 150                 155                 160

Ser Ser Arg Val Leu Leu Met Glu Glu Ala Lys Lys Ile Thr Phe Glu
                165                 170                 175

Leu Thr Val Lys Gln Leu Met Ser Phe Asp Pro Gly Glu Trp Ser Glu
                180                 185                 190

Ser Leu Arg Lys Glu Tyr Leu Leu Val Ile Glu Gly Phe Phe Ser Leu
            195                 200                 205

Pro Leu Pro Leu Phe Ser Thr Thr Tyr Arg Lys Ala Ile Gln Ala Arg
210                 215                 220

Arg Lys Val Ala Glu Ala Leu Thr Val Val Met Lys Arg Arg Glu
225                 230                 235                 240

Glu Glu Glu Glu Gly Ala Glu Arg Lys Lys Asp Met Leu Ala Ala Leu
                245                 250                 255

Leu Ala Ala Asp Asp Gly Phe Ser Asp Glu Glu Ile Val Asp Phe Leu
                260                 265                 270

Val Ala Leu Leu Val Ala Gly Tyr Glu Thr Thr Ser Thr Ile Met Thr
            275                 280                 285

Leu Ala Val Lys Phe Leu Thr Glu Thr Pro Leu Ala Leu Ala Gln Leu
            290                 295                 300

Lys Glu Glu His Glu Lys Ile Arg Ala Met Lys Ser Asp Ser Tyr Ser
305                 310                 315                 320

Leu Glu Trp Ser Asp Tyr Lys Ser Met Pro Phe Thr Gln Cys Val Val
                325                 330                 335

Asn Glu Thr Leu Arg Val Ala Asn Ile Ile Gly Gly Val Phe Arg Arg
                340                 345                 350
```

```
Ala Met Thr Asp Val Glu Ile Lys Gly Tyr Lys Ile Pro Lys Gly Trp
            355                 360                 365

Lys Val Phe Ser Ser Phe Arg Ala Val His Leu Asp Pro Asn His Phe
        370                 375                 380

Lys Asp Ala Arg Thr Phe Asn Pro Trp Arg Trp Gln Ser Asn Ser Val
385                 390                 395                 400

Thr Thr Gly Pro Ser Asn Val Phe Thr Pro Phe Gly Gly Gly Pro Arg
                405                 410                 415

Leu Cys Pro Gly Tyr Glu Leu Ala Arg Val Ala Leu Ser Val Phe Leu
            420                 425                 430

His Arg Leu Val Thr Gly Phe Ser Trp Val Pro Ala Glu Gln Asp Lys
        435                 440                 445

Leu Val Phe Phe Pro Thr Thr Arg Thr Gln Lys Arg Tyr Pro Ile Phe
    450                 455                 460

Val Lys Arg Arg Asp Phe Ala Thr
465                 470

(2) INFORMATION FOR SEQ ID NO: 3:

(i) SEQUENCE CHARACTERISTICS:
        (A) LENGTH: 4937 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Arabidopsis thaliana
        (B) STRAIN: cv. Columbia (vii) IMMEDIATE SOURCE:
        (A) LIBRARY: lambda gt10
        (B) CLONE: C204

(ix) FEATURE:
        (A) NAME/KEY: CDS
        (B) LOCATION:join(968..1483, 1680..1829, 1917..2165, 3903
            ..3989, 4084..4162, 4248..4354, 4446..4576, 4674
            ..4773)

(xi) SEQUENCE DESCRIPTION: SEQ ID NO: 3:

GGATCCAAAC AAAATGTAAT TATGGAACCA AAATTCTTGA CCTATGATTC ATCAGTTCCT      60

CCATTTCTCT ACAATAATTA ATATTCAATA AGAATTTCAC ATTAACATCC TTTTAATATA    120

TTTTAATTAT CTGTTGATGT CACTAGTTTG TTGATGCTAT CAACAAACCG ATCGATAATC    180

AATGGATTAA AATTGGTTCG ATTTCTTTTC ACTTAAGTGT CTTTTGAAGT TAGCTAAGTC    240

CAGTTACAAT CAAATTATCA TGACGAAATC AGAAGTTAAA AAAAAAAAAA AATCAGAAGT    300

TAAAAGTTGA ATAAATAATA TTTAGCATAT GCATGTGTGA GTTCTCTGCA ACCAAATACG    360

AAAACACACT AAACCATAAA CATTCTGGTT CCAAAAATAA ACGGAATAAA GCTACCGGAA    420

TTACTTTTTT ACCAGCAAAT GATATACAAT CCCAAATTAT ATAAATGATT CTACATATAG    480

TAAGAAAATC ATGATTCCAT TACCATGTGC ATAAAAGTTA ATAATATACA TAGACAACCC    540

ACAAATTCAT CTATATTTAC TATAATTAAT TTCGTACATG CCAAATATGT TTAGTTATA    600

ATACAGAAAA AATATAACTC TTTAAGGCAC TAAATCTTTT AAATTATAGA ATTTGCTCTC    660

TGATAAATTT GAAAATCTGT GTGTTAGAGA TGTTTGAAAC AAAATTTAGA ATAGTATCGA    720
```

-continued

```
AAATATTTTA TCCTTATTTA AAAAATTCAT ATTTTATGAA GAAGTTATTA TTCACTGCTT     780

ACTGTATTTT AGAAAATTAC TTATAATTTA GAAGAAAAAG AAAAGAAAAG AAGAAGAATG     840

CAAAAGAGTA TAATGATGAA AGGTCCTACT TTATGCAGAA ACCCCCCGTG TGCCCACTCT     900

CCCCTTCTCC ATTAATACTC TCTCTCCCTC ATCCTCTCTT CTTCTCTCAT CATCATCTTC     960

TTCTTCA ATG GCC TTC ACC GCT TTT CTC CTC CTC CTC TCT TCC ATC GCC     1009
        Met Ala Phe Thr Ala Phe Leu Leu Leu Leu Ser Ser Ile Ala
         1               5                  10

GCC GGC TTC CTC CTC CTA CTC CGC CGT ACA CGT TAC CGT CGG ATG GGT     1057
Ala Gly Phe Leu Leu Leu Leu Arg Arg Thr Arg Tyr Arg Arg Met Gly
 15              20                  25                  30

CTG CCT CCG GGA AGC CTT GGT CTC CCT CTG ATA GGA GAG ACT TTT CAG     1105
Leu Pro Pro Gly Ser Leu Gly Leu Pro Leu Ile Gly Glu Thr Phe Gln
             35                  40                  45

CTG ATC GGA GCT TAC AAA ACA GAG AAC CCT GAG CCT TTC ATC GAC GAG     1153
Leu Ile Gly Ala Tyr Lys Thr Glu Asn Pro Glu Pro Phe Ile Asp Glu
         50                  55                  60

AGA GTA GCC CGG TAC GGT TCG GTT TTC ATG ACG CAT CTT TTT GGT GAA     1201
Arg Val Ala Arg Tyr Gly Ser Val Phe Met Thr His Leu Phe Gly Glu
 65                  70                  75

CCG ACG ATT TTC TCA GCT GAC CCG GAA ACG AAC CGG TTT GTT CTT CAG     1249
Pro Thr Ile Phe Ser Ala Asp Pro Glu Thr Asn Arg Phe Val Leu Gln
     80                  85                  90

AAC GAA GGG AAG CTT TTT GAG TGT TCT TAT CCT GCT TCC ATT TGT AAC     1297
Asn Glu Gly Lys Leu Phe Glu Cys Ser Tyr Pro Ala Ser Ile Cys Asn
 95                 100                 105                 110

CTT TTG GGG AAA CAC TCT CTG CTT CTT ATG AAA GGT TCT TTG CAT AAA     1345
Leu Leu Gly Lys His Ser Leu Leu Leu Met Lys Gly Ser Leu His Lys
                 115                 120                 125

CGT ATG CAC TCT CTC ACC ATG AGC TTT GCT AAT TCT TCA ATC ATT AAA     1393
Arg Met His Ser Leu Thr Met Ser Phe Ala Asn Ser Ser Ile Ile Lys
             130                 135                 140

GAC CAT CTC ATG CTT GAT ATT GAC CGG TTA GTC CGG TTT AAT CTT GAT     1441
Asp His Leu Met Leu Asp Ile Asp Arg Leu Val Arg Phe Asn Leu Asp
         145                 150                 155

TCT TGG TCT TCT CGT GTT CTC CTC ATG GAA GAA GCC AAA AAG             1483
Ser Trp Ser Ser Arg Val Leu Leu Met Glu Glu Ala Lys Lys
 160                 165                 170

GTAACCAAAA AAATTCTTGC TTATCAAAAA CATTATATTA TTATTTTATT CGGCCTTCTC    1543

ACTTATGTTT TTTTTATAAT AAAAATAAAA TAAAAATCCC GGACCGAGTT TGTGACTCAG    1603

TGAGTCAGGC CGAGTCACCA CCGCATGCAT GCATGCATAG ATTGATGATT ATTAATGATG    1663

ATGATGTATG ATGCAG ATA ACG TTT GAG CTA ACG GTG AAG CAG TTG ATG       1712
                Ile Thr Phe Glu Leu Thr Val Lys Gln Leu Met
                         175                 180

AGC TTT GAT CCA GGG GAA TGG AGT GAG AGT TTA AGG AAA GAG TAT CTT     1760
Ser Phe Asp Pro Gly Glu Trp Ser Glu Ser Leu Arg Lys Glu Tyr Leu
     185                 190                 195

CTT GTC ATC GAA GGC TTC TTC TCT CTT CCT CTC CCT CTC TTC TCC ACC     1808
Leu Val Ile Glu Gly Phe Phe Ser Leu Pro Leu Pro Leu Phe Ser Thr
200                 205                 210                 215

ACT TAC CGC AAA GCC ATC CAA GTATATATTT CGTTTCATTT ACTAATTCTT         1859
Thr Tyr Arg Lys Ala Ile Gln
                 220

TCTTATTTCA ATCATATTTT GAGAATATAT ATCCTAATAT ATGTGTGTGT ATTTTAG      1916

GCG CGG AGG AAG GTG GCG GAG GCG TTG ACG GTG GTG GTG ATG AAA AGG     1964
Ala Arg Arg Lys Val Ala Glu Ala Leu Thr Val Val Val Met Lys Arg
         225                 230                 235
```

```
AGG GAG GAG GAG GAA GAA GGA GCG GAG AGA AAG AAA GAT ATG CTT GCG           2012
Arg Glu Glu Glu Glu Glu Gly Ala Glu Arg Lys Lys Asp Met Leu Ala
    240                 245                 250

GCG TTG CTT GCG GCG GAT GAT GGA TTT TCC GAT GAA GAG ATT GTT GAC           2060
Ala Leu Leu Ala Ala Asp Asp Gly Phe Ser Asp Glu Glu Ile Val Asp
255                 260                 265                 270

TTC TTG GTG GCT TTA CTT GTC GCC GGT TAT GAA ACA ACC TCC ACG ATC           2108
Phe Leu Val Ala Leu Leu Val Ala Gly Tyr Glu Thr Thr Ser Thr Ile
                275                 280                 285

ATG ACT CTC GCC GTC AAA TTT CTC ACC GAG ACT CCT TTA GCT CTT GCT           2156
Met Thr Leu Ala Val Lys Phe Leu Thr Glu Thr Pro Leu Ala Leu Ala
            290                 295                 300

CAA CTC AAG GTAATTTTCC CATTTTTGGT AAATAATCTC TCTACTTATT                   2205
Gln Leu Lys
        305

TATATACATG GTTCGTATTT AATTAATAAA GAATAACTTT GAGAAAAATA TTCGATTTTA         2265

GTATCGAATT TTGATTGAAT TATTTTTAAA AGAGTATACA CAGCGAATGA AAAACACGAC         2325

ACGTATGAAT GAAATTTTAG GTGTTATGTA GTTGGTTTGA TTGCGAATCA ACAAGATTTA         2385

GTGTTTTGGA AAAGATATTA AAAAATTAAG ATTCGATCTA TTCAGTGTTC ACTACATTGC         2445

ATCTCTGCAT GCAAACCGTT TTTTTGAAGG ACCACCGGCG CATGTTTTAC CCTGCTCTTG         2505

CTTTATTTGG GGTTTAGGGT ATCAAAACAA AAATGGTTTT GTTTCTTTTC TTTGAAAACT         2565

AATTAAATTA CATTTCTGTA CTTTCAACAA ATAACGAAA AGAGTGAAAA CATTGAATTA          2625

GAACACGGTG ATGTGTTGTT ATCAACTAAT ATGAACTTTT TCTTGTGGGC ACAATCTTAC         2685

TGATTTAAGC TTATTTCATT TTCTTAAGTA ATTAAGAGAT GGGAAGAAGT AGTTGGGGGA         2745

AAAATAAAAT TTAAGGTGAA AGAAAGAAAT GGGACAGAGA CTACAACAAT GGGAGCATAA        2805

TGATATGTGC ATGTTGGCCT CTAAATTTCT CCATCATTTA CGTTTCACAC GGGTGTCTAG        2865

ATTTTTTGGC AATTAATAAA AACTATTATA AAAAGGACAC ACACACATCA ATGAAACGGC        2925

TTAGGTCTCC AATGAACTAC TAGTTCACAT AGCAAGTAAG CAACAGTACA ATCTAGTCGG       2985

TTGATACTAA TAATTGATAG TAGCCAAAAA AAAAAGACTT TTTGTTTTTG GTTTAGAATA       3045

AGGTTTTTGT TTATAGCCTT CAATCTTGGT TAATTAATGG TTAGGTATCA AGAAAATTAA       3105

AATACGCGAC ATTAGCCGGG TAAGACGATC TAGTACTGCT ATTCACTATT TCAAATTATG       3165

TATATCATAT ACTAAACTGG TTTCAAAGTT TTTGTTTTCC GTCAACAAAT AATGAATTAG       3225

AAAACGTAAG CTTTCATTCT ATTTGTCTAT TCGATGAGTT TATAATCTAA GATTAAGCAT       3285

ATTATTAAGT GGGTGTGAGC TTTTTGAAAG GTGAAAACTG AAAAGTGTAA AAGGTACTAA       3345

AATTACCGTA AAAGTCAAAG TAGTCATTTT CGAAAATAGA CAACATCATC ACCTCAGTTT       3405

TAGAGTTTTA TTTTAATAAG GAAATTGTAA AATGTAAGGA GTTACAGTCT CAGAGATTTG       3465

ACTAATTTGT CTCCTGAACT GCATGCATAA TCACACTTTT ACCAAACCTC ATCTTCTTCT       3525

TTTGTTTTGT TTTGTTTGTT TGCCAACAAC TTTCATCTTC TTTTTTTATC TTACTTGTCC       3585

GATTATCCCC CAATAAATCT CTCTTTACAT TAAAGATAAA AGTTTATCA TAAATATGTT        3645

TGTGCTATGC GCGACCGACA AGCTTCTCAT CCATTGGTTC TTAATATTTT AATTATTTGT       3705

TGATGTCACT AGTTTTGTTC CAAGGATGGT ACTACTATAT TCACTAGTTT AGTCATTTAC       3765

TCATTAGTGC TTCGAATATG ACCAACCGGT TCAAAAAACG GTTGGACCGG TGACCTAATT       3825

AATTAATTTT GCTTTTACAC CTTGTTTCTT TCTTTTATTG TTGGTTGATT TGGTATTTGC       3885

TTGGTTGAAT ATAACAG GAA GAG CAT GAA AAG ATT AGG GCA ATG AAG AGT          3935
                Glu Glu His Glu Lys Ile Arg Ala Met Lys Ser
                                310                 315
```

| | |
|---|---|
| GAT TCG TAT AGT CTT GAA TGG AGT GAT TAC AAG TCA ATG CCA TTC ACA<br>Asp Ser Tyr Ser Leu Glu Trp Ser Asp Tyr Lys Ser Met Pro Phe Thr<br>320                       325                   330 | 3983 |
| CAA TGT GTAAGTGTAC TTACCTAAAG CTCTTAAGAA TTCTTGTCTT ATCTTCTTTC<br>Gln Cys | 4039 |
| TAGTCATTTC TCATCAGTAT CCTTATAAAC CTATTTTGAT TCAG GTG GTT AAT GAG<br>                                                                     Val Val Asn Glu<br>                                                                      335 | 4095 |
| ACG CTA CGA GTG GCT AAC ATC ATC GGC GGT GTT TTC AGA CGT GCA ATG<br>Thr Leu Arg Val Ala Asn Ile Ile Gly Gly Val Phe Arg Arg Ala Met<br>340                       345                   350 | 4143 |
| ACG GAT GTT GAG ATC AAA G GTAAAATAAT CTAACTTTTA AAATGAGTAA<br>Thr Asp Val Glu Ile Lys<br>355                   360 | 4192 |
| AAAGAGTCCA TTCTGTATCA AAAACTTAAC ATTTAGAAAA CTGGAACAAA ACCAG  GT<br>                                                                                              Gly | 4249 |
| TAT AAA ATT CCA AAA GGG TGG AAA GTA TTC TCA TCG TTT AGA GCG GTT<br>Tyr Lys Ile Pro Lys Gly Trp Lys Val Phe Ser Ser Phe Arg Ala Val<br>                  365                   370                   375 | 4297 |
| CAT TTA GAC CCA AAC CAC TTC AAA GAT GCT CGC ACT TTC AAC CCT TGG<br>His Leu Asp Pro Asn His Phe Lys Asp Ala Arg Thr Phe Asn Pro Trp<br>        380                   385                   390 | 4345 |
| AGA TGG CAG GTTTGTATTT TAAGCCCTGA ACTTGGTTTG GGTGTTCTTT<br>Arg Trp Gln<br>395 | 4394 |
| CTTTGCATTC TTGATTTTGA GTTATTGAAC GATTGCAATT CTGTGGAACA G AGC AAC<br>                                                                                            Ser Asn | 4451 |
| TCG GTA ACG ACA GGC CCT TCT AAT GTG TTC ACA CCG TTT GGT GGA GGG<br>Ser Val Thr Thr Gly Pro Ser Asn Val Phe Thr Pro Phe Gly Gly Gly<br>400                       405                   410 | 4499 |
| CCA AGG CTA TGT CCC GGT TAC GAG CTG GCT AGG GTT GCA CTC TCT GTT<br>Pro Arg Leu Cys Pro Gly Tyr Glu Leu Ala Arg Val Ala Leu Ser Val<br>415                       420                   425                   430 | 4547 |
| TTC CTT CAC CGC CTA GTG ACA GGC TTC AG GTATATATAC CTTCACATAG<br>Phe Leu His Arg Leu Val Thr Gly Phe Ser<br>                  435                   440 | 4596 |
| AAGATAGTAG CTCTGTTTTC CATTTCAAAA GGCTAAAGAG ACTGATTTGA TTTTGTTTTG | 4656 |
| TAAATTTGTT TGAACAG T TGG GTT CCT GCA GAG CAA GAC AAG CTG GTT TTC<br>                          Trp Val Pro Ala Glu Gln Asp Lys Leu Val Phe<br>                                 445                   450 | 4707 |
| TTT CCA ACT ACA AGA ACG CAG AAA CGG TAC CCG ATC TTC GTG AAG CGC<br>Phe Pro Thr Thr Arg Thr Gln Lys Arg Tyr Pro Ile Phe Val Lys Arg<br>                  455                   460                   465 | 4755 |
| CGT GAT TTT GCT ACT TGA AGAAGAAGAG ACCCATCTGA TTTTATTTAT<br>Arg Asp Phe Ala Thr *<br>        470 | 4803 |
| AGAACAACAG TATTTTTCAG GATTAATTTC TTCTTCTTTT TTTGCCTCCT TGTGGGTCTA | 4863 |
| GTGTTTGACA ATAAAAGTTA TCATTACTCT ATAAAGCCTT AGCTTCTGTG TACATAAAAA | 4923 |
| AAAAAAACTT TGTT | 4937 |

(2) INFORMATION FOR SEQ ID NO: 4:

(i) SEQUENCE CHARACTERISTICS:
        (A) LENGTH: 472 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ala Phe Thr Ala Phe Leu Leu Leu Ser Ser Ile Ala Ala Gly
 1               5                    10                  15

Phe Leu Leu Leu Arg Arg Thr Arg Tyr Arg Arg Met Gly Leu Pro
             20                  25                  30

Pro Gly Ser Leu Gly Leu Pro Leu Ile Gly Glu Thr Phe Gln Leu Ile
             35                  40                  45

Gly Ala Tyr Lys Thr Glu Asn Pro Glu Pro Phe Ile Asp Glu Arg Val
 50                  55                  60

Ala Arg Tyr Gly Ser Val Phe Met Thr His Leu Phe Gly Glu Pro Thr
 65                  70                  75                  80

Ile Phe Ser Ala Asp Pro Glu Thr Asn Arg Phe Val Leu Gln Asn Glu
                 85                  90                  95

Gly Lys Leu Phe Glu Cys Ser Tyr Pro Ala Ser Ile Cys Asn Leu Leu
                100                 105                 110

Gly Lys His Ser Leu Leu Leu Met Lys Gly Ser Leu His Lys Arg Met
                115                 120                 125

His Ser Leu Thr Met Ser Phe Ala Asn Ser Ser Ile Ile Lys Asp His
             130                 135                 140

Leu Met Leu Asp Ile Asp Arg Leu Val Arg Phe Asn Leu Asp Ser Trp
145                 150                 155                 160

Ser Ser Arg Val Leu Leu Met Glu Glu Ala Lys Lys Ile Thr Phe Glu
                165                 170                 175

Leu Thr Val Lys Gln Leu Met Ser Phe Asp Pro Gly Glu Trp Ser Glu
                180                 185                 190

Ser Leu Arg Lys Glu Tyr Leu Leu Val Ile Glu Gly Phe Phe Ser Leu
                195                 200                 205

Pro Leu Pro Leu Phe Ser Thr Thr Tyr Arg Lys Ala Ile Gln Ala Arg
210                 215                 220

Arg Lys Val Ala Glu Ala Leu Thr Val Val Met Lys Arg Arg Glu
225                 230                 235                 240

Glu Glu Glu Gly Ala Glu Arg Lys Lys Asp Met Leu Ala Ala Leu
                245                 250                 255

Leu Ala Ala Asp Asp Gly Phe Ser Asp Glu Glu Ile Val Asp Phe Leu
                260                 265                 270

Val Ala Leu Leu Val Ala Gly Tyr Glu Thr Thr Ser Thr Ile Met Thr
             275                 280                 285

Leu Ala Val Lys Phe Leu Thr Glu Thr Pro Leu Ala Leu Ala Gln Leu
             290                 295                 300

Lys Glu Glu His Glu Lys Ile Arg Ala Met Lys Ser Asp Ser Tyr Ser
305                 310                 315                 320

Leu Glu Trp Ser Asp Tyr Lys Ser Met Pro Phe Thr Gln Cys Val Val
                325                 330                 335

Asn Glu Thr Leu Arg Val Ala Asn Ile Ile Gly Val Phe Arg Arg
             340                 345                 350

Ala Met Thr Asp Val Glu Ile Lys Gly Tyr Lys Ile Pro Lys Gly Trp
             355                 360                 365

Lys Val Phe Ser Ser Phe Arg Ala Val His Leu Asp Pro Asn His Phe
370                 375                 380

Lys Asp Ala Arg Thr Phe Asn Pro Trp Arg Trp Gln Ser Asn Ser Val
385                 390                 395                 400

Thr Thr Gly Pro Ser Asn Val Phe Thr Pro Phe Gly Gly Gly Pro Arg
                405                 410                 415

Leu Cys Pro Gly Tyr Glu Leu Ala Arg Val Ala Leu Ser Val Phe Leu
```

-continued

```
                    420                 425                 430
His Arg Leu Val Thr Gly Phe Ser Trp Val Pro Ala Glu Gln Asp Lys
            435                 440                 445

Leu Val Phe Phe Pro Thr Thr Arg Thr Gln Lys Arg Tyr Pro Ile Phe
        450                 455                 460

Val Lys Arg Arg Asp Phe Ala Thr
465                 470
```

NUCLEIC ACID MOLECULES ENCODING CYTOCHROME P450-TYPE PROTEINS INVOLVED IN THE BRASSINOSTEROID SYNTHESIS IN PLANTS

The present invention relates to nucleic acid molecules encoding cytochrome P450-type proteins involved in the brassionosteroid synthesis in plants, to transgenic plant cells and plants containing such nucleic acid molecules as well as to processes for the identification of other proteins involved in brassinosteroid synthesis and processes for the identification of substances acting as brassinosteroids or as brassinosteroid inhibitors in plants.

In 1979 a novel plant growth-promoting factor, termed brassinolide, was isolated from the pollen of rape (*Brassica napus*) and identified as a novel type of steroid lactone. It was found that brassinolide-like steroid compounds (called brassinosteroids) occur in all plant species examined at very low concentrations (for review, see Mandava, Ann. Rev. Plant Physiol. Plant Mol. Biol. 39 (1988), 23–52). Initial studies of the physiological action of brassinolide showed that this particular factor (i) accelerated the germination and growth of plant seedlings at low temperatures, (ii) promoted the increase of cell size and elongation by induction of a longitudinal arrangement of cortical microtubuli and cellulose microfilaments on the surface of cells, (iii) promoted xylem differentiation by amplifying the tracheal elements, (iv) resulted in significant increase of dry weight of plants and their fruits, (v) promoted leaf unrolling and enlargement, (vi) induced H+ export and membrane hyperpolarization characteristic for auxin induced cell growth, (vii) inhibited the division of crown-gall tumour cells and radial growth of stems, (viii) repressed anthocyanin production in light-grown plants, (ix) inhibited the de-etiolation induced, e.g. by cytokinin in the dark, (x) promoted tissue senescence in the dark, but prolonged the life-span of plants in the light and (xi) induced plant pathogen resistance responses to numerous bacterial and fungal species (listed by Mandava (1988), loc. cit.).

Following the initial isolation of and physiological studies with brassinolides, numerous brassinosteroid compounds, representing putative biosynthetic intermediates, were identified in different plant species. Because the in vivo concentration of these compounds was found to be extremely low, efforts had been made to develop methods for chemical synthesis of these compounds (for review, see: Adam and Marquardt, Phytochem. 25 (1986), 1787–1799). These compounds were tested in field experiments using soybean, maize, rice and other crops as well as trees in order to confirm the results of physiological studies. However, the field trials showed that due to poor uptake of steroids through the plant epidermis, the amount of steroids required for spraying or fertilization was considerable. Several methods for the chemical synthesis of brassinolides had been described since then, however, their practical use in agriculture is rather limited. Because the prize of brassinolide treatments is comparably high, their application cannot compete with the application of other known fertilizers and pesticides. Thus, up to know the practical application of these compounds has largely been abandoned, except for their occassional application as crop safeners.

The interest in brassinosteroids as possible growth regulators has furthermore faded since plant physiologists claimed that physiological data did not indicate that these compounds were indeed functional growth factors because their concentrations in most plant species were very low in comparison to other growth factors, such as auxins, cytokinins, abscisic acid, ethylen and gibberellins. In addition, no plant mutant defective in brassinolide synthesis was available to demonstrate that these compounds are essential for plant growth and development. Therefore, brassinosteroids were classified as minor secondary plant metabolites with a questionable biological function.

In order to be able to demonstrate that brassinosteroids can indeed be used as potential growth regulators of plants and to exploit the possible advantages and potentials of these substances, it would be necessary to identify plant mutants defective in brassinosteroid synthesis which would allow the characterization of genes involved in brassinosteroid synthesis.

Thus, the problem underlying the present invention is to identify plant mutants defective in brassinosteroid synthesis and to identify nucleic acid molecules encoding proteins involved in the synthesis of brassinosteroids in plants.

The problem is solved by the provision of the embodiments characterized in the claims.

Thus, the invention relates to nucleic acid molecules encoding a protein having the biological, namely the enzymatic, activity of a cytochrome P450-type hydroxylase or encoding a biologically active fragment of such a protein. Such nucleic acid molecules encode preferably a protein that comprises the amino acid sequence shown in Seq ID No. 2 or a fragment thereof that has the biological activity of a cytochrome P450-type hydroxylase. More preferably such nucleic acid molecules comprise the nucleotide sequence shown in Seq ID No. 1, namely the indicated coding region, or a corresponding ribonucleotide sequence.

The present invention also relates to nucleic acid molecules coding for a protein having the amino acid sequence as coded for by the exons of the nucleotide sequence given in SEQ ID NO:3 or coding for a fragment of such a protein, wherein the protein and the fragment have the biological activity of a cytochrome P450 hydroxylase. In particular, the present invention relates to nucleic acid molecules comprising the nucleotide sequence depicted in SEQ ID NO:3, namely the nucleotide sequence of the indicated exons, or a corresponding ribonucleotide sequence. Furthermore, the present invention relates to nucleic acid molecules which hybridize to any of the nucleic acid molecules as described above and which code for a protein having the biological activity of a cytochrome P450-type hydroxylase or for a biologically active fragment of such a protein as well as to nucleic acid molecules which are complementary to any of the nucleic acid molecules as described above. The present invention also relates to nucleic acid molecules encoding a cytochrome P450-type hydroxylase, or a biologically active fragment thereof, the sequence of which differs from the sequence of the above-described nucleic acid molecules due to the degeneracy of the genetic code.

By "hybridizing" it is meant that such nucleic acid molecules hybridize under conventional hybridization conditions, preferably under stringent conditions such as described by, e.g, Sambrook et al. (Molecular Cloning; A Laboratory Manual, 2nd Edition, Cold Spring Harbor Laboratory Press, Cold Spring Harbor, N.Y. (1989)). Nucleic acid molecules hybridizing with the above-described nucleic acid molecules can in general be derived from any plant possessing such molecules, preferably from monocotyledonous or dicotyledonous plants, in particular from any plant of interest in agriculture, horticulture or wood culture, such as crop plants, namely those of the family Poaceae, any other starch producing plants, such as potato, maniok, leguminous plants, oil producing plants, such as oilseed rape, linenseed, etc., plants using protein as storage substances, such as soybean, plants using sucrose as storage substance, such as sugar beet or sugar cane, trees, ornamental plants etc. Preferably the nucleic acid molecules according to the invention are derived from plants belonging to the family Brassicaceae. Nucleic acid molecules hybridizing to the above-described nucleic acid molecules can be isolated, e.g., from libraries, such as cDNA or genomic libraries by techniques well known in the art. For example, hybridizing nucleic acid molecules can be identified and isolated by using the above-described nucleic acid molecules or fragments thereof or complements thereof as probes to screen libraries by hybridizing with said molecules according to standard techniques. Possible is also the isolation of such nucleic acid molecules by applying the polymerase chain reaction (PCR) using as primers oligonucleotides derived from the above-described nucleic acid molecules.

The term "hybridizing nucleic acid molecules" also includes fragments, derivatives and allelic variants of the above-described nucleic acid molecules that code for a protein having the biological activity of a cytochrome P450-type hydroxylase or a biologically active fragment thereof. Fragments are understood to be parts of nucleic acid molecules long enough to code for the described protein or a biologically active fragment thereof. The term "derivative" means in this context that the nucleotide sequence of these nucleic acid molecules differs from the sequences of the above-described nucleic acid molecules in one or more positions and are highly homologous to said nucleic acid molecules. Homology is understood to refer to a sequence identity of at least 40%, particularly an identity of at least 60%, preferably more than 80% and still more preferably more than 90%. The deviations from the sequences of the nucleic acid molecules described above can, for example, be the result of substitutions, deletions, additions, insertions or recombination. Homology further means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same biological function. They may be naturally occuring variations, such as sequences from other plant varieties or species, or mutations. These mutations may occur naturally or may be obtained by mutagenesis techniques. Furthermore, these variations may be synthetically produced sequences. The allelic variations may be naturally occuring variants as well as synthetically produced or genetically engineered variants.

The proteins encoded by the various derivatives and variants of the above-described nucleic acid molecules share specific common characteristics, such as enzymatic activity, molecular weight, immunological reactivity, conformation, etc., as well as physical properties, such as electrophoretic mobility, chromatographic behaviour, sedimentation coefficients, pH optimum, temperature optimum, stability, solubility, spectroscopic properties, etc.

Cytochrome P450 proteins can be characterized by several features. For example, they are membrane-associated NAD(P)H dependent monooxygenases which normally form in vivo a complex with reductases. The CO-complex of these proteins shows an absorption maximum in the range of 450 nm.

The proteins encoded by the nucleic acid molecules according to the invention comprise preferably domains characteristic for cytochrome P450 proteins, especially those characteristic for microsomal cytochrom P450 proteins, such as the conserved N-terminal membran-anchoring domain, the proline rich domain, the heme-binding domain and the oxygen-binding domain (see, for example, Nebert and Gonzalez, Ann. Rev. Biochem. 56 (1987), 945–993). Furthermore, it is preferred that the proteins encoded by the nucleic acid molecules according to the invention contain domains characteristic for steroid hydroxylases, namely steroid binding domains. Preferably the proteins have the enzymatic activity of a steroid hydroxylase.

In a preferred embodiment the nucleic acid molecules according to the invention encode a cytochrome P450-type protein with the enzymatic activity of a hydroxylase which is involved in the conversion of cathasterone to teasterone (see FIG. 1). This enzymatic activity may be determined by feeding experiments as described in the examples.

The proteins encoded by the nucleic acid molecules according to the invention which, due to the presence of certain domains and due to their enzymatic activity can be classified as cytochrome P450 proteins, display overall a very low homology to known cytochrome P450s (less than 40%). Thus, these proteins are novel and constitute a new family of cytochrome P450 proteins with a novel substrate specificity.

The nucleic acid molecules according to the invention are preferably RNA or DNA molecules, preferably cDNA or genomic DNA.

The present invention is based on the finding that a particular Arabidopsis mutant generated by gene-tagging, which showed dwarfism and several other morphological and developmental abnormalities, can be restored to the wildtype phenotype by the addition of specific brassinosteroid compounds. Furthermore, the mutated gene and a corresponding cDNA had been isolated and characterized as encoding a cytochrome P450-type hydroxylase, the overexpression of which in the tagged mutant can also restore the wildtype phenotype. Moreover, it has been found that overexpression of the cDNA in transgenic plants leads to several physiological and phenotypic changes which might be useful for the engineering of improved plants for agriculture, wood culture or horticulture.

The present invention provides evidence that the described nucleic acid molecules encode proteins with an enzymatic activity involved in brassinosteroid synthesis in plants. Furthermore, the present invention shows that a mutant defective in this enzyme activity shows severe physiological and phenotypic changes, for example, dwarfism, which can be reverted by addition of specific brassinosteroid compounds, and that plants overexpressing such an enzyme activity also show phenotypic changes, such as increased cell elongation.

Thus, the present invention for the first time clearly establishes that brassinosteroids are indeed of central importance as plant growth regulators and, furthermore, provides extremely useful tools to (i) identify mutants deficient in brassinosteroid snythesis;

(ii) identify and isolate genes encoding proteins involved in the brassionosteroid synthesis in plants or in its regulation;

(iii) generate plants with modified brassinosteroid synthesis and consequently with modified physiological and/or phenotypic characteristics; and (iv) identify compounds which may act as potential brassionosteroids on plants.

The different possible applications of the nucleic acid molecules according to the invention as well as molecules derived from them will be described in detail in the following.

In one aspect the present invention relates to nucleic acid probes which specifically hybridize with a nucleic acid molecule as described above. This means that they hybridize, preferably under stringent conditions, only with the nucleic acid molecules as described above and show no or very little cross-hybridization with nucleic acid molecules coding for other proteins. The nucleic acid probes according to the invention comprise a nucleic acid molecule of at least 15 nucleotides. Nucleic acid probe technology is well known to those skilled in the art who will readily appreciate that such probes may vary in length. The nucleic acid probes are useful for various applications. On the one hand, they may be used as PCR primers for amplification of nucleic acid molecules according to the invention. On the other hand, they can be useful tools for the detection of the expression of molecules according to the invention in plants, for example, by in-situ hybridization or Northern-Blot hybridization. Other applications are the use as hybridization probe to identify nucleic acid molecules hybridizing to the nucleic acid molecules according to the invention by homology screening of genomic or cDNA libraries. Nucleic acid probes according to the invention which are complementary to an RNA molecule as described above may also be used for repression of expression of such an RNA due to an antisense effect or for the construction of appropriate ribozymes which specifically cleave such RNA molecules. Furthermore, the person skilled in the art is well aware that it is also possible to label such a nucleic acid probe with an appropriate marker for specific applications.

The present invention also relates to vectors, particularly plasmids, cosmids, viruses, bacteriophages and other vectors used conventionally in genetic engineering that contain a nucleic acid molecule according to the invention.

In a preferred embodiment the nucleic acid molecule present in the vector is linked to regulatory elements which allow the expression of the nucleic acid molecule in procaryotic or eucaryotic cells. Expression comprises transcription of the nucleic acid molecule into a translatable mRNA. Regulatory elements ensuring expression in procaryotic or eucaryotic cells are well known to those skilled in the art. In the case of eucaryotic cells they comprise normally promoters ensuring initiation of transcription and optionally poly-A signals ensuring termination of transcription and stabilization of the transcript. Additional regulatory elements may include transcriptional as well as translational enhancers.

The present invention furthermore relates to host cells comprising a vector as described above or a nucleic acid molecule according to the invention wherein the nucleic acid molecule is foreign to the host cell.

By "foreign" it is meant that the nucleic acid molecule is either heterologous with respect to the host cell, this means derived from a cell or organism with a different genomic background, or is homologous with respect to the host cell but located in a different genomic environment than the naturally occuring counterpart of said nucleic acid molecule. This means that, if the nucleic acid molecule is homologous with respect to the host cell, it is not located in its natural location in the genome of said host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally.

The host cell can be any procaryotic or eucaryotic cell, such as bacterial, fungal, plant or animal cells. Preferred fungal cells are, for example, those of the genus Saccharomyces, in particular those of the species *S. cerevisiae*.

The present invention furthermore relates to proteins encoded by the nucleic acid molecules according to the invention or to fragments of such proteins which have the biological activity of a cytochrome P450-type hydroxylase.

Furthermore, the present invention relates to antibodies specifically recognizing proteins according to the invention or parts, i.e specific fragments or epitopes, of such proteins. Specific eptitopes or fragments may, for example, comprise amino acid sequences which constitute domains which are characteristic for the proteins according to the invention, such as the substrate binding domain or the like. These antibodies can be monoclonal antibodies, polyclonal antibodies or synthetic antibodies as well as fragments of antibodies, such as Fab fragments etc. These antibodies can be used, for example, for the immunoprecipitation and immunolocalization of proteins according to the invention as well as for the monitoring of the synthesis of such proteins, for example, in recombinant organisms, and for the identification of proteins interacting with the proteins according to the invention.

Another subject of the invention is a process for the preparation of such proteins which comprises the cultivation of host cells according to the invention which, due to the presence of a vector or a nucleic acid molecule according to the invention, are able to express such a protein, under conditions which allow expression of the protein and recovering of the so-produced protein from the culture. Depending on the specific constructs and conditions used, the protein may be recovered from the cells, from the cultur medium or from both. For the person skilled in the art it is well known that it is not only possible to express a native protein but also to express the protein as fusion proteins or to add signal sequences directing the protein to specific compartments of the host cell, ensuring secretion of the protein into the culture medium, etc.

The nucleic acid molecules according to the invention are in particular useful for the genetic manipulation of plant cells in order to modify the brassinosteroid synthesis and to obtain plants with modified, preferably with improved or useful phenotypes. Thus, the present invention relates also to transgenic plant cells which contain stably integrated into the genome a nucleic acid molecule according to the invention linked to regulatory elements which allow for expression of the nucleic acid molecule in plant cells and wherein the nucleic acid molecule is foreign to the transgenic plant cell. For the meaning of foreign, see supra.

The presence and expression of the nucleic acid molecule in the transgenic plant cells leads to the synthesis of a protein with the biological activity of a cytochrome P450-type hydroxylase which has an influence on brassinosteroid synthesis in the plant cells and leads to physiological and phenotypic changes in plants containing such cells.

Thus, the present invention also relates to transgenic plants comprising transgenic plant cells according to the invention.

Due to the expression of a protein having the biological activity of a cytochrome P450-type hydroxylase this transgenic plants may show various physiological, developmental and/or morphological modifications in comparison to wildtype plants. For example, these transgenic plants may display an increased induction of pathogenesis related genes (see, for example, Uknes et al., Plant Cell 4 (1992), 645–656), modified morphology, namely a stimulation of growth, increased cell elongation and/or increased wood production due to stimulated xylem differentiation. Furthermore, these transgenic plants may show accelarated seed germination at low temperatures, an increase in dry weight, repressed anthocyanin production during growth in light and/or inhibited de-etiolation which is induced, e.g. by cytokinin, in the dark.

The provision of the nucleic acid molecules according to the invention furthermore opens up the possibility to produce transgenic plant cells with a reduced level of the cytochrome P450-type hydroxylase as described above and, thus, with a defect in brassinosteroid synthesis. Techniques how to achieve this are well known to the person skilled in the art. These include, for example, the expression of antisense-RNA, ribozymes, of molecules which combine antisense and ribozyme functions and/or of molecules which provide for a cosupression effect.

When using the antisense approach for reduction of the above described enzymatic activity in plant cells, the nucleic acid molecule encoding the antisense-RNA is preferably is of homologous origin with respect to the plant species used for transformation. However, it is also possible to use nucleic acid molecules which display a high degree of homology to endogenously occuring nucleic acid molecules encoding the respective enzyme activity. In this case the homology is preferably higher than 80%, particularly higher than 90% and still more preferably higher than 95%.

The reduction of the synthesis of a protein according to the invention in the transgenic plant cells results in an alteration in the brassinosteroid synthesis and/or metabolism in the cells. In transgenic plants comprising such cells this can lead to various physiological, developmental and/or morphological changes.

Thus, the present invention also relates to transgenic plants comprising the above-described transgenic plant cells. These may show, for example, morphological changes, such as dwarfism, and/or developmental changes in comparison to wildtype plants, such as a reduced elongation of the hypocotyl of seedlings germinating in the dark or male sterility. Furthermore, these plants may display physiological changes in comparison to wildtype plants, such as an altered stress tolerance. Preferably the transgenic plants according to the invention show at least one of the following features:

- the seedlings which result from germination in the dark have a short hypocotyl, no apical hook, open cotyledons and/or extended leaf primordia when compared to wildtype seedlings;
- the length of epidermal cell files in the hypocotyl is reduced about 5-fold when compared to wildtype plants;
- the length of epidermal cell files in the roots of the seedlings is decreased by about 20 to 50% when compared to wildtype plants;
- the epidermal cells of the hypocotyl show thick transverse files of cellulose fibers (see, for example, FIGS. 2D,E);
- the epidermal cells of the hypocotyl show perpendicular divisions leading to differentiation of stomata guard cells (FIG. 2B),
- the cotyledons show dense stomata and trichomes normally characteristic for leaves (FIG. 2C);
- derepression of photomorphogenesis and de-etiolation in the dark;
- a 20 to 30-fold reduction in size in comparison to wildtype plants when grown in soil under white light (dwarfism);
- a reduction of the number of longitudinal mesophyll cell files in leaves and a failure of palisade cells to elongate;
- an amplification and duplication of stomatal guard cells in the leaf epidermis (FIGS. 2F,G);
- unequal division of cambium in the stem;
- production of extranumerary phloem cell files at the expense of xylem cells;
- the failure of the pollen to elongate during germination thereby resulting in male sterility;
- a differential regulation of stress responsive genes.

The present invention also relates to cultured plant tissues comprising transgenic plant cells as described above which either show overexpression of a protein according to the invention or a reduction in synthesis of such a protein.

In yet another aspect the invention also relates to harvestable parts and to propagation material of the transgenic plants according to the invention which either contain transgenic plant cells expressing a nucleic acid molecule according to the invention or which contain cells which show a reduced activity of the described protein. Harvestable parts can be in principle any useful parts of a plant, for example, leaves, stems, fruit, seeds, roots etc.

Propagation material includes, for example, seeds, fruits, cuttings, seedlings, tubers, rootstocks etc.

For the expression of the nucleic acid molecules according to the invention in sense or antisense orientation in plant cells, the molecules are placed under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells. To obtain expression in all tissues of a transgenic plant, preferably constitutive promoters are used, such as the 35 S promoter of CaMV (Odell et al., Nature 313 (1985), 810–812) or promoters of the polyubiquitin genes of maize (Christensen et al., Plant Mol. Biol. 18 (1982), 675–689). In order to achieve expression in specific tissues of a transgenic plant it is possible to use tissue specific promoters (see, e.g., Stockhaus et al., EMBO J. 8 (1989), 2245–2251). Known are also promoters which are specifically active in tubers of potatoes or in seeds of different plants species, such as maize, Vicia, wheat, barley etc. Inducible promoters may be used in order to be able to exactly control expression. An example for inducible promoters are the promoters of heat shock proteins.

The regulatory elements may further comprise transcriptional and/or translational enhancers functional in plants cells.

Furthermore, the regulatory elements may include transcription termination signals, such as a poly-A signal, which lead to the addition of a poly A tail to the transcript which may improve its stability.

In the case that a nucleic acid molecule according to the invention is expressed in sense orientation it is in principle possible to modifiy the coding sequence in such a way that the protein is located in any desired compartment of the plant cell. These include the endoplasmatic reticulum, the vacuole, the mitochondria, the plastides, the apoplast, the cytoplasm etc. Methods how to carry out this modifications and signal sequences ensuring localization in a desired compartment are well known to the person skilled in the art.

Methods for the introduction of foreign DNA into plants are also well known in the art. These include, for example, the transformation of plant cells or tissues with T-DNA using Agrobacterium tumefaciens or Agrobacterium rhizogenes (EP-A 120 516; EP-A 116 718; Hoekema in: The Binary Plant Vector System, Offsetdrukkerij Kanters BV, Alblasserdam (1985), Chapter V; Fraley et al., Crit. Rev. Plant Sci. 4, 1–46 und An et al., EMBO J. 4 (1985), 277–287), the fusion of protoplasts, direct gene transfer (see, e.g., EP-A 164 575), injection, electroporation, biolistic methods like particle bombardment and other methods.

The transformation of most dicotyledonous plants is possible with the methods described above. But also for the transformation of monocotyledonous plants several successful transformation techniques have been developed. These include the transformation using biolistic methods (Wan and Lemaux, Plant Physiol. 104 (1994), 37–48; Vasil et al., Bio/Technology 11 (1993), 1553–1558), protoplast transformation, electroporation of partially permeabilized cells, introduction of DNA using glas fibers, etc.

In general, the plants which can be modified according to the invention and which either show overexpression of a protein according to the invention or a reduction of the synthesis of such a protein can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc.

The present invention furthermore provides a process for the identification and isolation of nucleic acid molecules encoding proteins which are involved in brassinosteroid synthesis in plants or in its regulation which comprises the steps of:

(a) screening naturally occurring, artificially mutagenised or genetically engineered dwarf mutants for those whose seedlings upon germination in the dark display no or only little elongation of the hypocotyl;

(b) identifying those dwarf mutants identified in step (a) in which elongation of the hypocotyl in the dark can be stimulated by adding different brassinosteroids or brassinosteroid-like compounds;

(c) identification and isolation of the gene(s) which are capable of complementing those dwarf mutants identified in step (b);

(d) characterization of the isolated gene(s) and its (their) encoded product(s).

This process is based on the finding that mutants which are defective in brassinosteroid synthesis show the characteristic features of reduced growth (dwarfism) and a reduced elongation of the hypocotyl in seedlings grown in the dark when compared to wildtype plants. By these features it is possible to select plant mutants which may have a defect in brassinosteroid synthesis. This can be confirmed if it possible to complement the mutant phenotype by addition of brassinosteroid compounds (step (b)). Various brassinosteroid compounds are known to the person skilled in the art. They may be naturally occuring brassinosteroids or chemically synthesized analogs. The way of application of the brassinosteroid compounds to the plants is not critical. Spraying of solutions is preferred. From the identified mutants which are indeed defective in brassinosteroid synthesis, the mutated gene can be identified and isolated.

One possibility is: (i) to create a plurality of mutants by gene-tagging (e.g. by T-DNA or transposons), (ii) identify according to step (a) and (b) the mutants which are defective in brassinosteroid synthesis, (iii) to prepare a genomic library of the and (iv) to isolate the mutated gene with the help of the DNA used for tagging of the genes. This leads to the identification of the tagged mutated gene. This can subsequently be used to isolate wildtype cDNA and genomic clones using standard techniques, for example, hybidization techniques or PCR. Such an approach is in principle described in the examples, see supra.

Alternatively, the identification and isolation of the mutated gene can be carried out as follows: (i) precise genetic mapping of the mutation which allows then (ii) the isolation of yeast artificial chromosome (YAC) clones carrying the corresponding gene on a smaller chromosome fragment, (iii) using these YAC clones to isolate corresponding cosmid clones, (iv) using these cosmid clones for the genetic complementation of the mutation, (v) identifying those cosmid clones which can complement the mutation and (vi) isolating with the help of the cosmid clone the corresponding cDNA and/or genomic sequences. This procedure is generally known as genomic walking and is well known to the person skilled in the art.

The identified and isolated genes and/or cDNAs can subsequently be characterized according to standard techniques, such as restriction mapping and sequencing. The biologigal activity of the encoded product may be determined by homology comparisons with known proteins, in vivo feeding assays of the mutant etc.

In a preferred embodiment the above-described process is carried out with transgenic plants showing reduced activity of the enzyme according to the invention which had been generated with the above-described nucleic acid molecules, for example, by expressing an antisense-RNA.

The described process, thus, allows to identify nucleic acid molecules which encode a protein having the same enzymatic properties as the protein according to the invention and which is, thus, able to complement a mutant defective in this protein, even though the nucleic acid molecule encoding the protein may not hybridize to the nucleic acid molecules described above.

Thus, the present invention also relates to nucleic acid molecules obtainable by the above-described process. In principle, any nucleic acid molecule encoding a protein involved in brassinosteroid synthesis or in its regulation may be identified by this method as long as its mutation leads to dwarfism and reduction of hypocotyl elongation in the dark. Preferably such nucleic acid molecules encode proteins involved in one or more enzymatic step(s) of the brassinosteroid synthesis pathway, and more preferably proteins which show the same enzymatic properties as the proteins according to the invention.

By the provision of the knowledge that plant mutants defective in brassinosteroid synthesis may be identified by the features that they display dwarfism and reduced elongation of the hypocotyl of seeds germinating in the dark, the present invention allows to establish a simple method for identifying chemical compounds which can act like brassinosteroids in plants and which therefore may constitute potential growth factors in plants.

Thus, the present invention also provides a method for the identification of chemical compounds which can act as brassinosteroids in plants comprising the steps of:

(a) contacting a transgenic plant according to the invention which show a reduced activity of the protein according to the invention, or a mutant as identified by steps (a) and (b) of the method described above, which show a defect in brassinosteroid synthesis, with a plurality of chemical compounds; and (b) determining those compounds which are capable of compensating in the plants or mutants as defined in (a) the effects that resulted from defects in the brassinosteroid synthesis.

Plants used in step (a) of this method may be plants which show reduced activity of the proteins according to the invention and, thus, have a defect in brassinosteroid synthesis which leads to dwarfism and reduced elongation of the hypocotyl of seedlings germinating in the dark. Alternatively, other plant mutants may be used which had been identified as being defective in brassinosteroid synthesis since they display dwarfism and reduced elongation of the hypocotyl in the dark and can be restored to the wildtype phenotype by addition of specific brassinosteroids.

Chemical compounds which can partly or fully restore the wildtype phenotype may constitute potential growth factors for plants.

In another aspect the present invention also relates to a method for the identification of chemical compounds which can act as brassinosteroids in plants comprising the steps of:

(a) contacting germinating seeds of a plant according to the invention which show a reduced activity of the protein according to the invention and thus a defect in brassinosteroid synthesis, or of a dwarf mutant the seedlings of which show reduced elongation of the hypocotyl in the dark and in which normal growth can be restored by addition of specific brassinosteroids, with a plurality of chemical compounds; and (b) determining those compounds which are capable of restoring normal growth of the hypocotyl and/or roots in the seedlings.

Furthermore, the present invention relates to a method for the identification of chemical compounds which can act as inhibitors of brassinosteroids or can suppress the biological activities of brassinosteroids comprising the steps of:

(a) contacting plant cells or plants overexpressing a nucleic acid molecule according to the invention and, thus, showing a modified brassinosteroid synthesis and the above-described physiological and/or phenotypic changes, with a plurality of chemical compounds; and (b) identifying those compounds which lead to a weakening of the effects which resulted from altered brassinosteroid synthesis in these cells or plants.

The present invention also relates to a method for the identification of chemical compounds which can act as inhibitors of brassinosteroids or can suppress the biological activities of brassinosteroids comprising the steps of:

(a) contacting germinating seedlings of a plant according to the invention which show reduced activity of the protein according to the invention and, thus, a defect in brassinosteroid synthesis, or of a dwarf mutant the seedlings of which show reduced elongation of the hypocotyl in the dark and in which normal growth can be restored by addition of specific brassinosteroids, with brassinosteroids which are capable of restoring normal elongation of the hypocotyl of the seedlings germinating in the dark and simultaneously with a plurality of chemical compounds; and (b) determining those compounds which compete with the brassinosteroids to restore normal elongation of the hypocotyl.

Inhibitors identified by the two above-described methods may prove useful as herbicides, pesticides or safeners.

Beside the above described possibilities to use the nucleic acid molecules according to the invention for the genetic engineering of plants with modified characteristics and their use to identify homologous molecules, the described nucleic acid molecules may also be used for several other applications, for example, for the identification of nucleic acid molecules which encode proteins which interact with the cytochrome P450-type hydroxylase described above. This can be achieved by assays well known in the art, for example, by use of the so-called yeast "two-hybrid system". In this system the protein encoded by the nucleic acid molecules according to the invention or a smaller part thereof is linked to the DNA-binding domain of the GAL4 transcription factor. A yeast strain expressing this fusion protein and comprising a lacZ reporter gene driven by an appropriate promoter, which is recognized by the GAL4 transcription factor, is transformed with a library of cDNAs which will express plant proteins fused to an activation domain. Thus, if a protein encoded by one of the cDNAs is able to interact with the fusion protein comprising the P450 protein, the complex is able to direct expression of the reporter gene. In this way the nucleic acid molecules according to the invention and the encoded cytochrome P450 can be used to identify proteins interacting with the cytochrome P450, such as protein kinases, protein phosphatases, NAD (P)H oxidoreductases and/or cytochrome b5 proteins which are known to interact in plants and animals with cytochrome P450 proteins. Other methods for identifying proteins which interact with the proteins according to the invention or nucleic acid molecules encoding such molecules are, for example, the in vitro screening with the phage display system as well as filter binding assays.

Furthermore, is it possible to use the nucleic acid molecules according to the invention as molecular markers in plant breeding as well as for the generation of modified cytochrome P450 proteins, as, e.g., proteins with an altered substrate specifity.

Moreover, the nucleic acid molecules and proteins according to the invention can be used for the production of teasterone in any desired recombinant organism such as bacteria, fungi, animals or plants.

Furthermore, the overexpression of nucleic acid molecules according to the invention may be used for the alteration or modification of plant/insect or in general plant/pathogen interactions. The term pathogen includes, for example, bacteria and fungi as well as protozoa.

The nucleic acid molecules according to the invention as well as the encoded proteins and the brassinosteroid compounds identified by a method according to the invention can also be used for the regulation of stem and leaf (as well as other plant organ) development, which includes the regulation of the proportion of phloem and xylem in all crops and trees, namely in those plants which are of interest in wood production.

A further possible use of the nucleic acid molecules, proteins and brassionosteroid compounds identified by a method according to the invention is the regulation of the differentiation and of the number of stomatal guard cells which may be of interest in the breeding or genetic engineering of plants with better stress tolerance, including drought, osmotic and other stresses.

FIG. 1 shows the biosynthesis pathway of brassinosteroids (Fujioka et al., Biosci. Biotech. Biochem. 59 (1995), 1543–1547).

FIG. 2 illustrates the effects of the cpd mutation on seedling development in the dark and light.

(A) In the dark the cpd mutant (right) exhibits short hypocotyl and open cotyledons, whereas the hypocotyl is elongated and the hook of cotyledons is closed in the wild type (left). (B) Unusual cell division and guard cell differentiation in the hypocotyl epidermis and (C) closely spaced stomata in the cotyledon epidermis of the cpd mutant. In contrast to wild type (D), the length of epidermal cells is reduced in the cpd mutant (E) and their surface is covered by transverse cellulose microfibrils (labeled by black arrows). In comparison to wild type (F), the adaxial leaf epidermis of the cpd mutant (G) shows straight cell walls and duplicated stomatal structures. In the light (H) the cpd mutant (left) is smaller than the wild type (right), due to inhibition of longitudinal growth in all organs (close up of mutant in I). Cross sections of wild type (J) and cpd mutant (K) leaves show differences in the size and elongation of mesophyll cells. Comparison of the organization of phloem (p) and xylem (x) cell files in stem cross sections of wild type (L) and cpd mutant (M) plants. D–E, F–G, J–K and L–M are identical magnifications. Scale bars label 200 μm in D and 100 μm in J and L.

FIG. 3 illustrates the altered patterns of gene expression in the cpd mutant and CPD overexpressing plants in the dark and light.

(A) Hybridization of RNAs prepared from wild type (left) and cpd mutant (right) plants, grown in media with 15 mM sucrose for 5 weeks in the dark, with RBCS, CAB and UBI gene probes. (B) RNAs were prepared from wild type (wt), cpd mutant (cpd) and genetically complemented cpd (cpd comp.) seedlings grown in glass jars under white light for 2 weeks and hybridized with the RBCS, CAB, alkaline peroxidase (APE), superoxide dismutase (SOD), gluthatione-S-transferase (GST), heat-shock 70 (HSP70), lignin-forming peroxidase (LPE), chalcone synthase (CHS), lipoxygenase (LOX2), S-adenosyl-methionine synthase (SAM), heat-shock 18.2 (HSP18.2), alcohol dehydrogenase (ADH), and pathogenesis related PR1, PR2 and PR5 gene probes. To control an equal loading of RNA samples, the blots were hybridized with the UBI gene probe (data not shown). The effects of light, cytokinin and sucrose on the level of steady-state CPD RNA was assayed by transferring 10 days old wild type seedlings (grown in white light and in the presence of 15 mM sucrose) to media containing either 0.1% (3 mM) or 3% (90 mM) sucrose. These seedlings were further grown for 6 days in either dark (D) or light (L), with ($D^+$ and $L^+$) or without (D and L) cytokinin (1.5 μM 6(γ,γ-dimethylallylamino)-purine riboside) before RNA isolation.

FIG. 4 shows schematically the chromosomal localization, physical structure and transcription of wild type and T-D NA tagged CPD alleles.

(A) Schematic genetic linkage map of Arabidopsis chromosome 5 (top line), showing the position of the T-DNA insertion and cpd mutation in relation to those of ttg (transparent testa glabra), co (constans), hy5 (long hypocotyl) and ASA1 (anthranylate synthase) loci. The second line shows the location of a YAC contig carrying the CPD gene. Schematic structure of the CPD gene, as well as the position of the T-DNA insertion in the cpd allele, are shown in the middle. The promoter of the CPD gene is labeled by an arrow, exons are shown as thick black bars. The structure of the T-DNA insert is compared to that of the T-DNA of Agrobacterium transformation vector pPCV5013Hyg. The T-DNA insertion consists of two DNA segments (T-DNA1 and T-DNA2), carrying respectively part of the octopine synthase (ocs) gene and the hpt selectable marker gene in inverse orientation, as compared to the map of pPCV5013Hyg vector. Lines above the schematic map of the CPD gene and below the map of T-DNA insertion indicate restriction endonuclease cleavage sites. Abbreviations: cM, centiMorgan; ocs, octopine synthase gene, ocsδ, octopine synthase gene segment, hpt, hygromycin phosphotransferase gene, pBR, pBR322 plasmid replicon; ori, replication origin of pBR322; pg5, promoter of T-DNA gene 5; pnos, nopaline synthase promoter, Lb and Rb, left and right border sequences of the T-DNA; B, BamHI; H, HindIII, P, PstI, R, EcoRI and K, KpnI. (B) RNAs prepared from wild type cell suspension culture (c), wild type and cpd mutant seedlings (s) were hybridized with the PstI-HindIII plant DNA-T-DNA junction fragment flanking the hpt-pBR segment (T-DNA2). RNAs prepared from seedlings and different organs of soil-grown plants were hybridized with the CPD cDNA as probe. Abbreviation: stem infl., inflorescence stems.

Figure 5A:
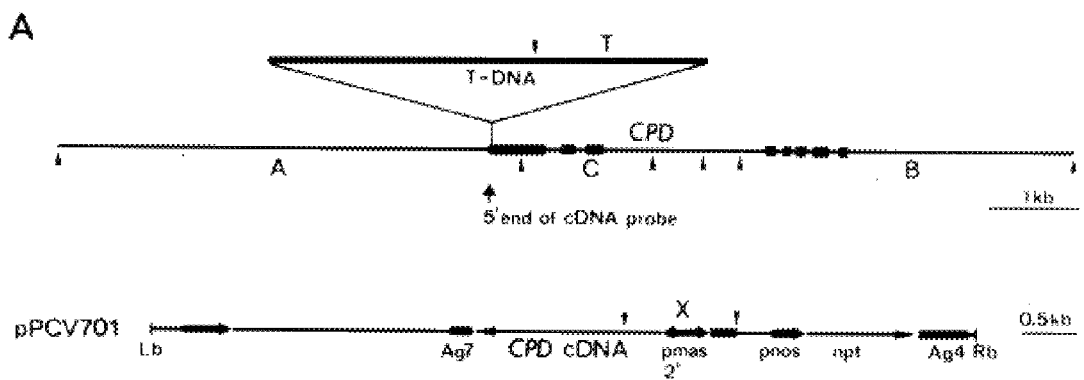

FIG. 5 shows the genetic complementation of the cpd mutation.

(A) Schematic maps of the T-DNA-tagged cpd gene and the T-DNA of plant gene expression vector pPCV701, carrying the CPD cDNA driven by the mas 2' promoter.

HindIII cleavage sites are indicated by black arrows below the map of the cpd gene and above the map of pPCV701 expression vector. Fragments A, B and C indicate HindIII fragments of the wild type CPD gene hybridizing with the CPD cDNA probe. T labels the T-DNA-plant DNA junction fragment that hybridizes with the cDNA probe in the cpd mutant. X labels the HindIII fragment carrying the junction of the mas 2' promoter and CPD cDNA. Because the 5'-end of the cDNA probe is located very close to the site of T-DNA insertion in the cpd gene, the cDNA probe did not detect the second T-DNA- plant DNA junction fragment, carrying part of the "A" fragment linked to the T-DNA. Abbreviations: Lb and Rb, left and right borders of the T-DNA of pPCV701 expression vector, pmas, promoter of the mannopine synthase gene; pnos, nopaline synthase promoter; npt, kanamycin resistance (neomycin phosphotransferase) gene; Ag7 and Ag4, polyadenylation sequences derived from T-DNA genes 4 and 7, respectively. (B) Left: Southern hybridization of HindIII digested DNAs from wild type, cpd mutant and a CPD overexpressing complemented line with the CPD cDNA probe. The DNA fingerprints show the presence of the mas promoter-cDNA junction (X) and cpd specific fragments (B,C and T), as well as the absence of the wild type target site (A) in the complemented (cpd compl.) and cpd mutant lines. Other fragments detected by the cDNA probe correspond to 6 new T-DNA border fragments. Thus, the genetic segregation and DNA fingerprinting data indicate that in the complemented line tandem T-DNA copies of pPCV701 vector are present in 3 loci showing independent segregation. Right RNAs were prepared from 14 days old wild type, cpd mutant and complemented cpd plants and hybridized with the CPD cDNA probe. (C) Top: Comparison of the phenotype of wild type (left) and complemented cpd seedlings grown in soil under white light. Bottom: Comparison of the leaf morphology of wild type (first 2 leaves from the left) to that of cpd mutant (third leaf) and CPD overexpressing complemented plants (three leaves at the right).

Figure 6A:
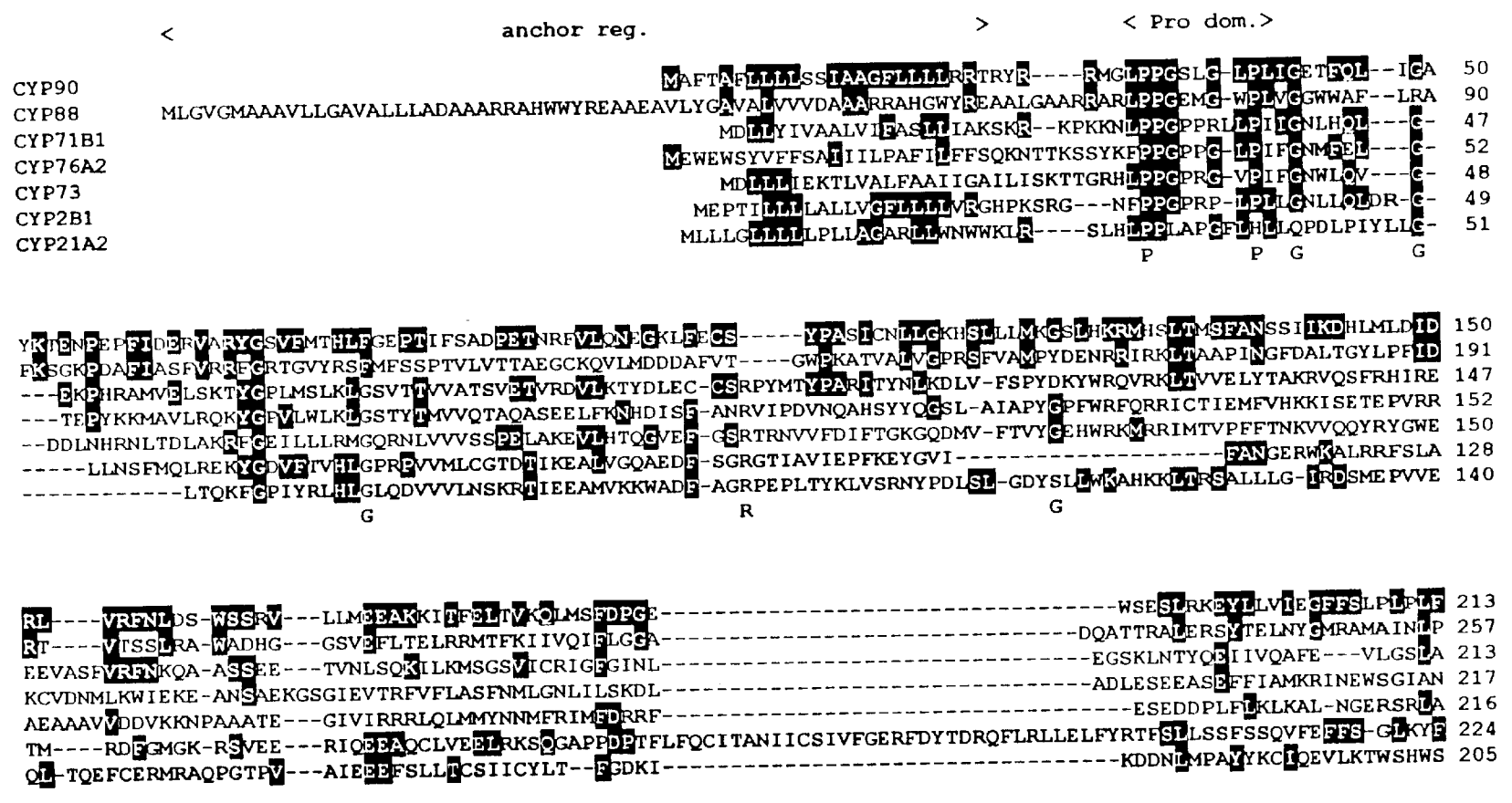
Figure 6B:
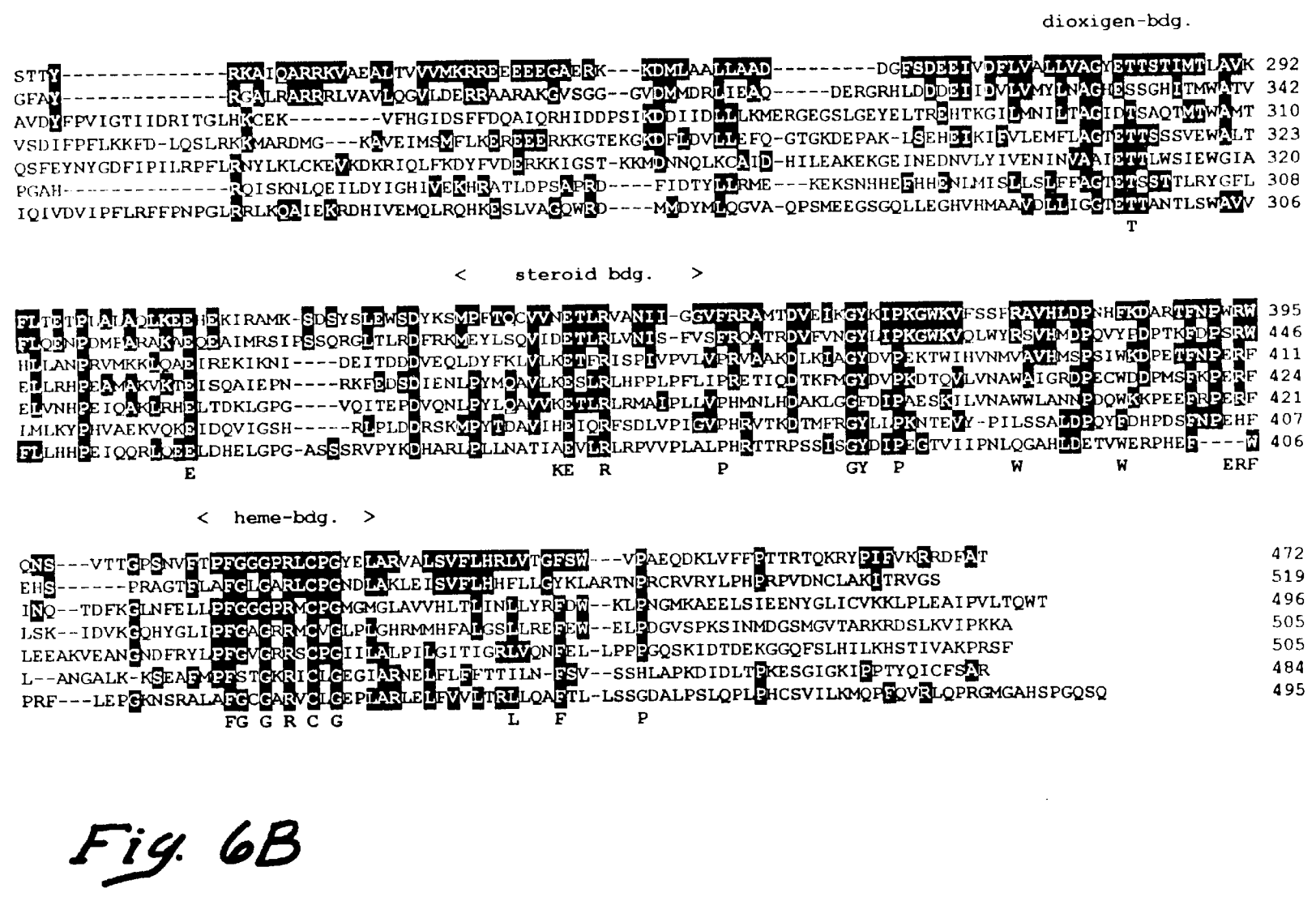

FIG. 6 demonstrates the sequence homology between CYP90 and other cytochrome P450 proteins from plants and animals.

CYP90 shows the highest sequence identity (28%) with CYP88 ($GA_{12}$→$GA_{53}$ gibberellin 13-hydroxylase; Winkler and Helentjaris, Plant Cell 7 (1995), 1307–1317) from maize, but differs in several domains from other plant P450s, including CYP71B1 of *Thlaspi arvense* (23% identity, GenBank (gb) L24438), CYP76A2 of eggplant (19% identity, gb X71657) and cinnamate 4-hydroxylase CYP73 of Jerusalem artichoke (17% identity, gb Z17369). CYP90 and CYP88 differ from all other plant P450s (Frey et al., Mol. Gen. Genet. 246 (1995), 100–109) by amino acid exchanges in the conserved positions $G_{76}$, $K_{337}$, $P_{350}$, $W_{375}$, $W_{384}$, $E_{393}$, and $F_{396}$, as indicated below the sequence comparison. CYP90 also exhibits sequence homology to all conserved domains of animal P450s, such as CYP2B1 (gb J00719) and CYP21A2 (gb S29670), and also to the central variable region of CYP2 family (positions 135–249) which carries the substrate-binding domains SRS2 and SRS3 (Gotoh, J. Biol. Chem. 267 (1992), 83–90). The locations of conserved domains of microsomal P450s, including the membrane anchor region, proline rich-domain, as well as the $O_2$-, steroid-, and heme-binding domains are indicated by arrows above the aligned sequences. Identical amino acids are labeled by inverted printing.

Figure 7:
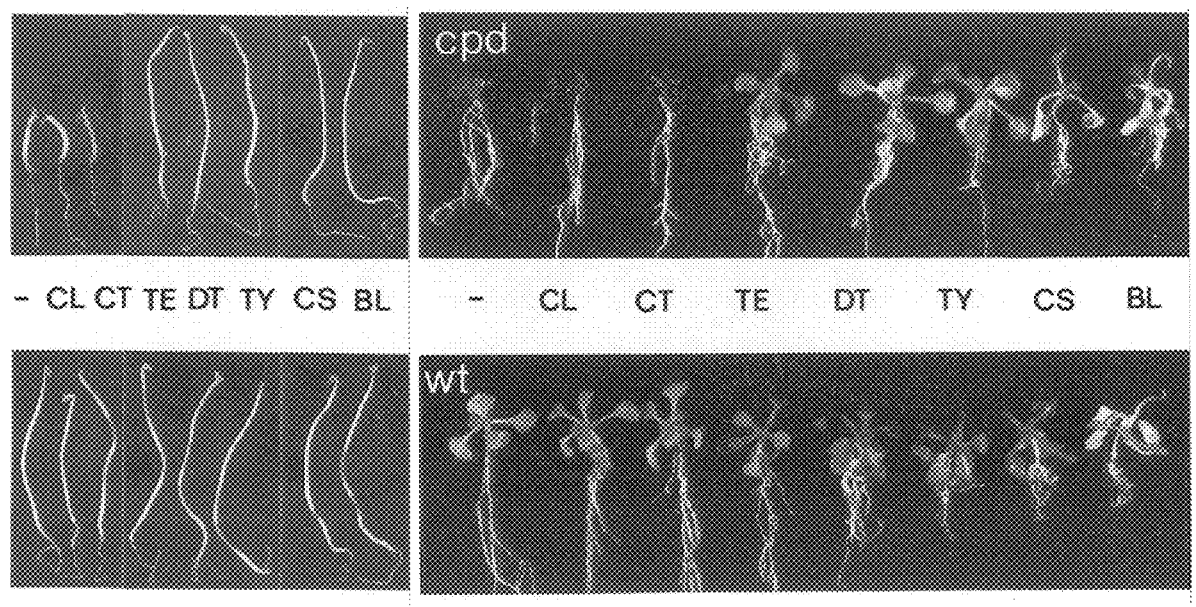

FIG. 7 shows the restoration of the cpd mutant phenotype to wild type by complementation with brassinosteroids.

Wild type (wt) and cpd mutant seedlings were grown for 5 days in the dark (left) or for 14 days in the light (right) with no steroid (−), or with $0.2 \times 10^{-6}$M of campesterol (CL), cathasterone (CT), teasterone (TE), 3-dehydrotesterone (DT), typhasterol (TY), castasterone (CS) or brassinolide (BL).

Figure 8:
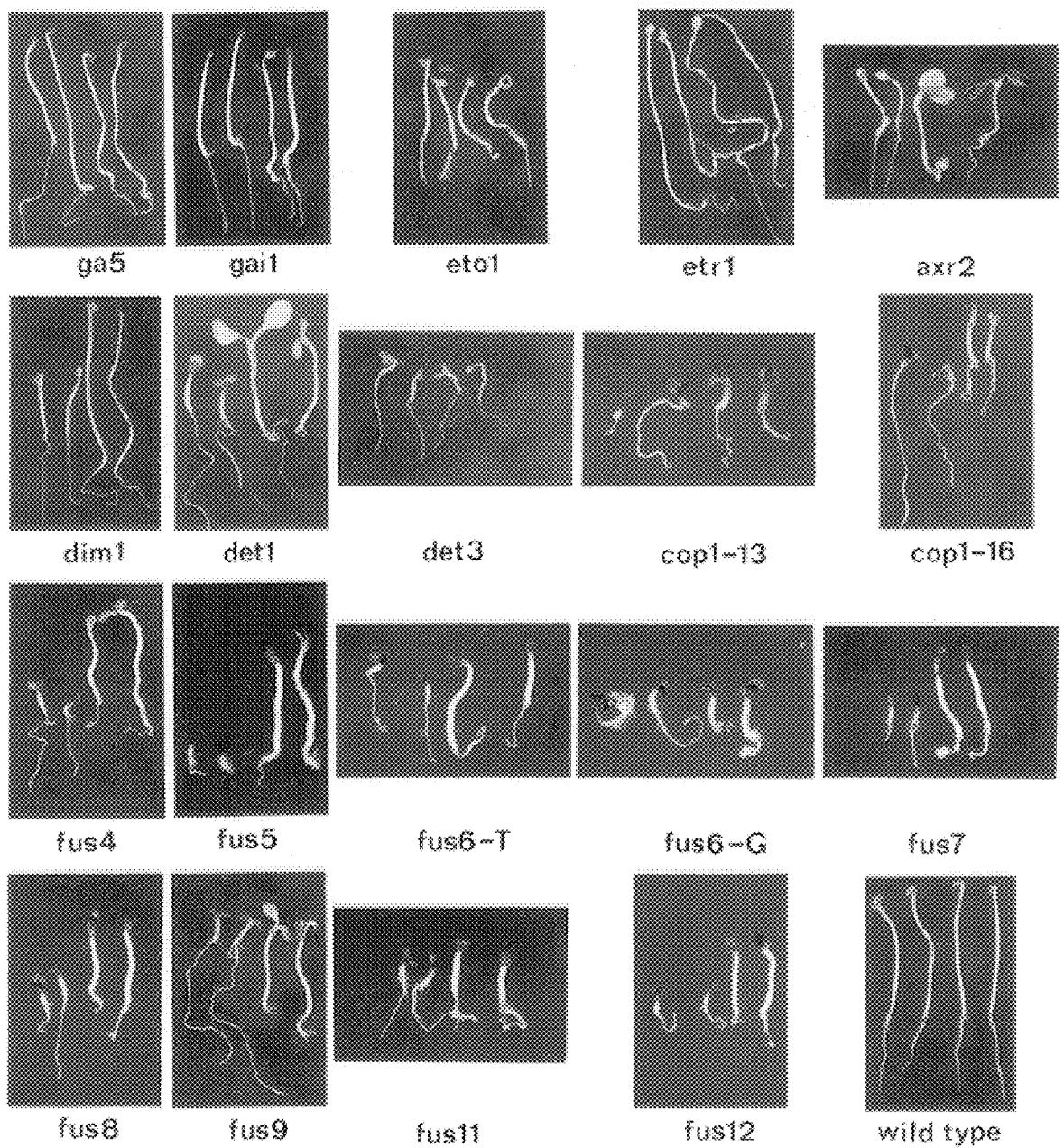

FIG. 8 shows the effect of brassinosteroids on the hypocotyl elongation of dark-grown Arabidopsis mutants.

Each picture shows seedlings grown for 5 days in the dark. From left to right, the first seedling was grown in the absence of steroid, the second was treated with ergosterol, the third with epi-castasterone and the fourth with epi-brassinolide. The concentration of steroids was $0.1 \times 10^{-6}$M. (Before taking the pictures the seedlings were inspected under the microscope, which explains the greening of cotyledons in certain mutants.)

The Examples illustrate the description.

EXAMPLE 1

Construction And Identification Of T-DNA Tagged Mutant Impaired In The Regulation Of Cell Elongation And Skotomorphogenic Development A genetic technology, using the transferred DNA (T-DNA) of *Agrobacterium tumefaciens* Ti plasmid as an insertional mutagen, was developed for induction of gene mutations by gene tagging in higher plants. Namely, tissue culture transformation of *Arabidopsis thaliana* was carried out with a modified Ti plasmid derived vector, i.e. pPCV5013Hyg, as described in Koncz et al. (Proc. Natl. Acad. Sci. USA 86 (1989), 8467–8471), Koncz et al. (Plant Mol. Biol. 20 (1992b), 963–976) and Koncz et al. (Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1–22)). This gene tagging technology was applied, using the model plant *Arabidopsis thaliana*, for generation of a collection of T-DNA insertional mutants, in order to identify mutations and corresponding genes, controlling plant development, in particular cell growth in different plant organs.

Figure 2A:
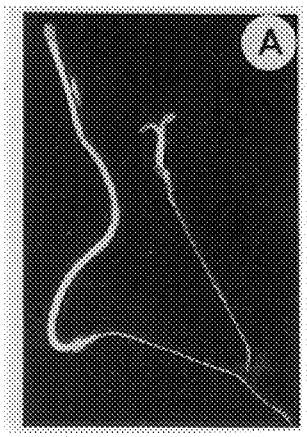
Figures 2B, 2C:
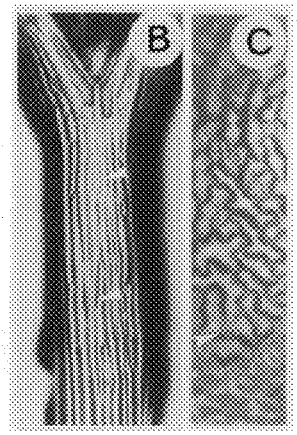
Figures 2D, 2E:
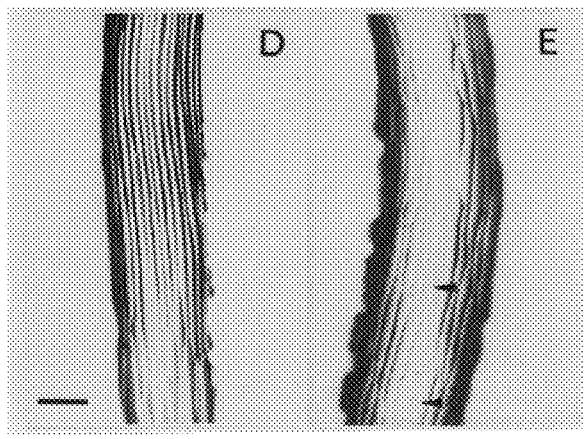
Figure 3A:
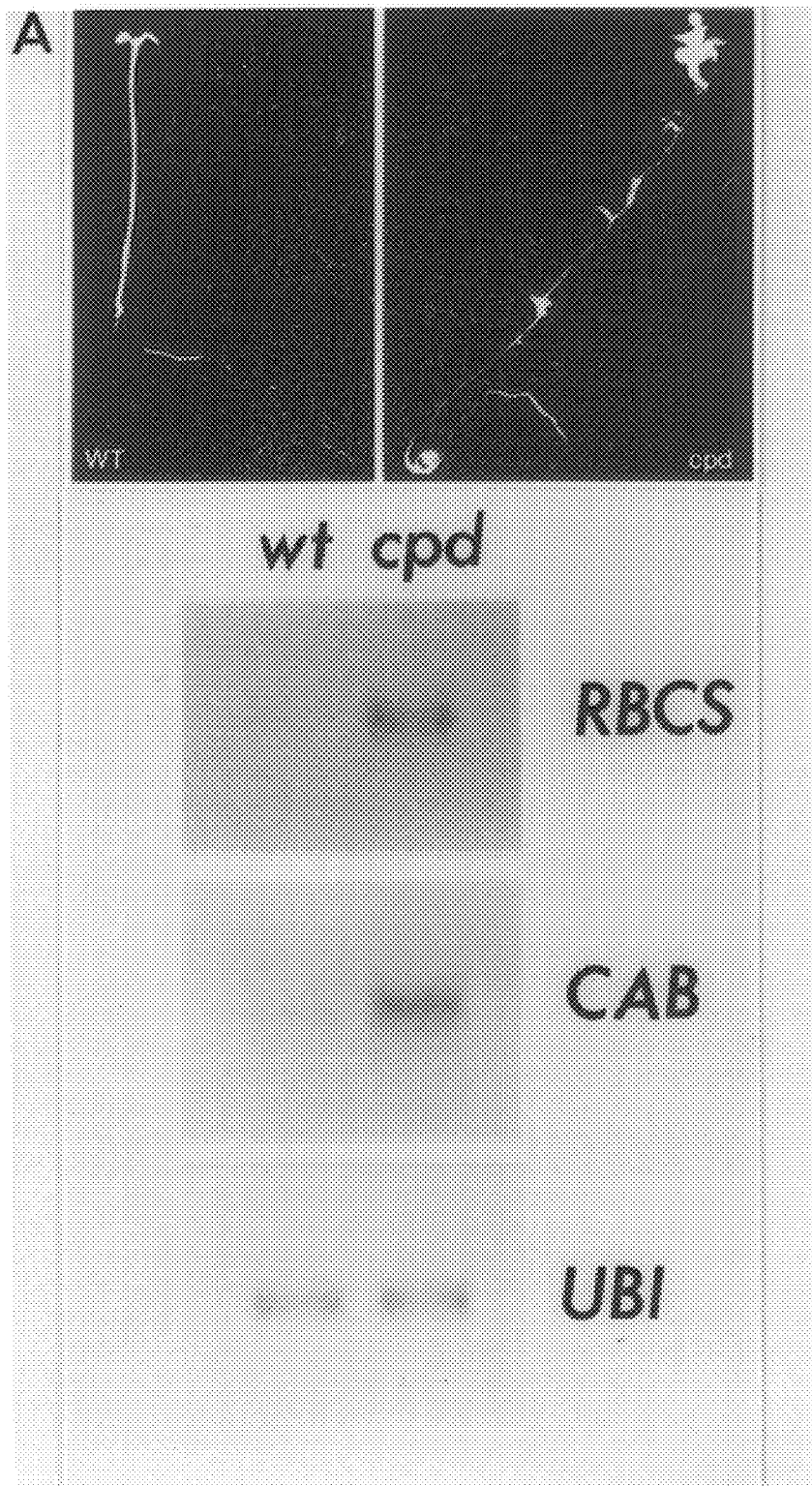

By screening for mutants defective in hypocotyl and/or root elongation during skotomorphogenesis, a recessive mutation causing constitutive photomorphogenesis and dwarfism (cpd) was identified. Unlike the wild type, the cpd mutant developed a short hypocotyl, no apical hook, open cotyledons, and extended leaf primordia in the dark (FIGS. 2A,B). As compared to wildtype, the length of epidermal cell files was reduced at least 5-fold in the hypocotyl, but decreased only by 20 to 50% in the root of mutant seedlings. Epidermal cells of the mutant hypocotyl were decorated by thick transverse files of cellulose microfibrils (FIGS. 2D,E) and showed perpendicular divisions leading to differentiation of stomatal guard cells (FIG. 2B). Dense stomata and trichomes characteristic for leaves were also observed on the epidermis of mutant cotyledons (FIG. 2C). During growth for 5 weeks in the dark the mutant developed numerous rosette leaves, while wild type seedlings opened their cotyledons without leaf expansion under these conditions (FIG. 3 A). These phenotypic traits indicated a derepression of photomorphogenesis and de-etiolation in the dark-grown cpd mutant. Hybridization of steady-state RNAs prepared from these seedlings, using an ubiquitin (UBI) gene probe as an internal control, confirmed that morphological signs of de-etiolation in the mutant were accompanied by an increase in the expression of light-regulated genes, coding for the small subunit of ribulose 1,5-bisphosphate carboxylase (RBCS) and the chlorophyll a/b-binding protein (CAB, FIG. 3A).

Figures 2F, 2G:
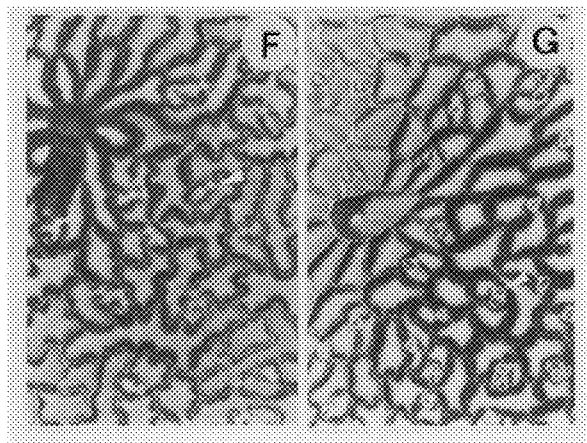
Figures 2H, 2I:
Figures 2J, 2K:
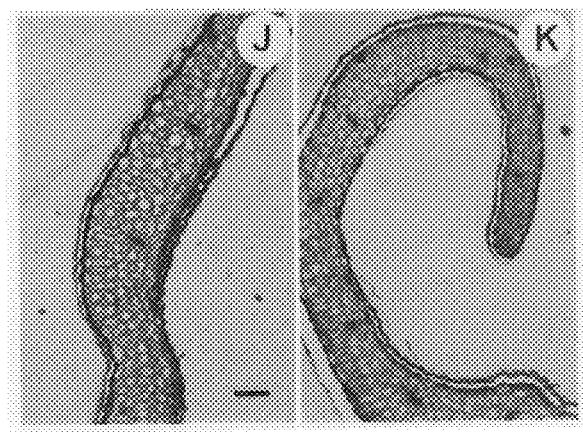
Figures 2L, 2M:
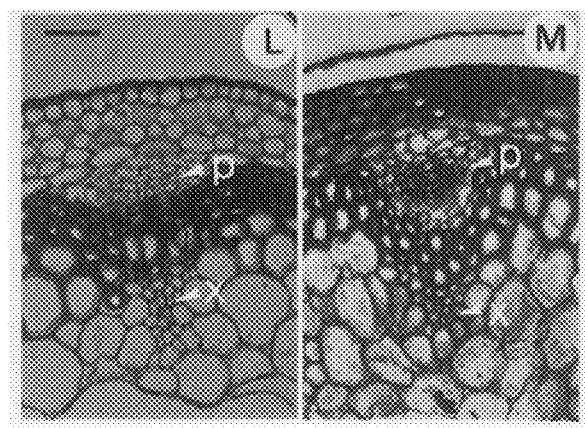

When grown in soil under white light, the size of cpd mutant plants was 20 to 30-fold smaller than that of the same age wild type plants. Exposure to light induced greening and chloroplast differentiation in the periderm of mutant roots (data not shown) and resulted in a further inhibition of cell elongation, leading to an overall reduction of the length of petioles, leaves, inflorescence-stems and flower organs (FIGS. 2H,I). Histological analysis showed that in the round-shape epinastic mutant leaves the number of longitudinal mesophyll cell files was reduced and the palisade cells failed to elongate (FIGS. 2J,K). The cell walls were straightened in the adaxial leaf epidermis of the mutant, which displayed an amplification and duplication of stomatal guard cells (FIGS. 2F,G). Stem cross sections showed an unequal division of cambium, producing extranumerary phloem cell files at the expense of xylem cells in the mutant (FIGS. 2L,M). The cpd mutant was viable in soil and produced eggs and pollen of wild type size. However, the mutant did not set seeds because its pollen failed to elongate during germination, resulting in male sterility.

EXAMPLE 2

Genetic Analysis Of The cpd Mutation

For trisomic analysis and linkage mapping a cpd/+ line was crossed with the tester lines as described (Koncz et al. (1992b), loc. cit.) and hygromycin resistant F1 hybrids were selected by germinating seeds in MSAR medium (Koncz et al. (1994), loc. cit.).

After outcrossing of the mutant with wild type, the cpd mutation co-segregated with a single T-DNA insertion, carrying a hygromycin resistance (hpt) marker gene from the Agrobacterium transformation vector pPCV5013Hyg (Koncz et al. (1989)', loc. cit.). The cpd mutation and the T-DNA insertion were mapped to chromosome 5-14.3 (FIG. 4A), using trisomic testers and the ttg marker of chromosome 5 in repulsion as described in the following.

After outcrossing of the cpd mutant with wild type, 8 F2 families yielded an offspring of 1297 wild type and 437 dwarf plants (2.97:1), fitting ($c^2$ 0.037, homogeneity: 2,599; P=0.85) the expected 3:1 ratio for monogenic segregation of the recessive cpd mutation. From these F2 families, 5383 mutants were tested on hygromycin and all displayed resistance, indicating a tight linkage between the T-DNA insertion and the cpd mutation.

In contrast to other trisomic hybrids, segregating the mutation at a ratio of 3:1, the chromosome 5 trisomic tester T31 produced an aberrant F2 ratio of 588 wild type (336 resistant and 252 sensitive to hygromycin) and 60 cpd mutant (all hygromycin resistant) plants. The ratios of wild type to mutant (9.8:1) and hygromycin resistant to sensitive (1.57:1) progeny matched with the ratios expected for synteny ($\geq 8:1$ and between 1.25:1 and 2.41:1, respectively).

The T-DNA insert and the cpd mutation were simultaneously mapped, using the ttg marker of chromosome 5 in repulsion. For determination of the cpd-ttg map distance, two mapping populations were raised, one including plants grown in soil and another using seedlings germinated in MSAR medium and tested in the presence of 15 μg/ml hygromycin. The soil-grown population was scored for the hairless ttg and dwarf cpd phenotypes in F2 and seeds from fertile plants were carried to full-F3 analysis. By labeling cpd as "a" and ttg as "b", the actual scores in the soil-grown population were 1054 AaBb, 685 aaB. (424 aaBB and 261 aaBb by extrapolation), 387 AAbb, 261 aAbb, 248 AaBB, 251 AABb, 21 AABB and 25 aabb. Progeny analysis showed that the AaBb, aAbb, AaBB and aabb classes were hygromycin resistant, in contrast to the hygromycin sensitive classes AAbb, AABb and AABB. In the population scored on MSAR medium with controlled seed germination the data were 815 AaB., 512 aaB., 193 AAB., 300 AAbb, 159 aAbb and 17 aabb. Both mapping populations yielded identical frequencies for the double recombinant fraction (cpd-ttg). The recombination frequencies and derived map distances were calculated by the maximum likelihood method as described (Koncz et al., Methods in Arabidopsis Research; Singapore, World Scienticic, 1992a). From these data the smaller map distance, corrected for the error resulting from uneven seed germination in soil, was accepted, resulting in 21.18±0.86 cM for the cpd(5-14.3)-ttg(5-35.5) interval. By scoring 1520 recombinant chromosomes, no crossing-over between the T-DNA-encoded hygromycin resistance marker and the cpd mutation was found, indicating that the T-DNA insertion was located in the cpd locus.

Figure 4A:
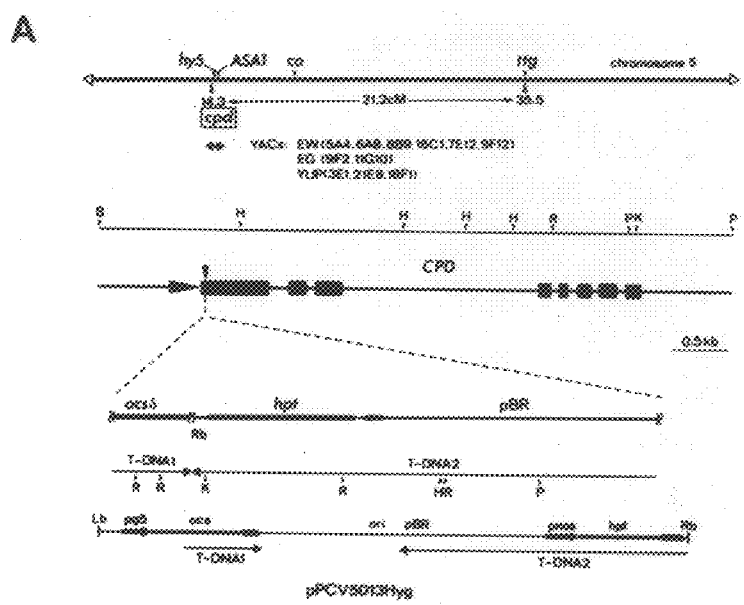

The physical map of the T-DNA-tagged locus was determined by DNA hybridization and showed that the cpd mutant contained a T-DNA insert of 4.8 kb, which underwent internal rearrangements (FIG. 4A).

EXAMPLE 3

Isolation Of The T-DNA Tagged Locus As Well As Wildtype cDNAs And Genomic DNAs Of The Cpd Locus To isolate the T-DNA-tagged locus, a genomic DNA library was constructed by ligation of cpd DNA, digested partially by MboI, into the BamHI site of the λEMBL 3 vector (Sambrook et al. (1989), loc. cit.). The T-DNA-tagged locus was isolated by constructing a genomic DNA library from the cpd mutant and mapped by hybridization with T-DNA derived probes (FIG. 4A).

The T-DNA/plant DNA insert junctions were subcloned, sequenced and used as probes to determine precisely the genomic location of the T-DNA insertion by isolation of Arabidopsis YAC (yeast artificial chromosome) clones. The YAC clones (FIG. 4A) overlapped with the ASA1 (anthranylate synthase, chr5-14.7) and hy5 (long hypocotyl locus, chr5-14.8) region of chromosome 5 (R. Schmidt, unpublished; Hauge et al., Plant J. 3 (1993), 745–754), thus matching the map position (chr5-14.3) determined for the T-DNA-tagged cpd mutation by genetic linkage analysis.

Figure 4B:

Plant DNA sequences flanking the hpt-pBR segment of T-DNA (FIG. 4A) hybridized with a mRNA of 1.7 kb present in wildtype seedlings and cell suspension cultures, but failed to detect any transcript in the cpd mutant (FIG. 4B).

Following the physical mapping of the λEMBL3 clones, the T-DNA-plant DNA juntion fragments (flanked by BamHI and HindIII sites in the plant DNA, FIG. 4A) were used as probes for the isolation of 4 genomic and 4 cDNA clones from wildtype Arabidopsis λEMBL4 genomic and λgt10 cDNA libraries. To identify yeast artificial chromosome clones containing the CPD locus, wildtype Arabidopsis YAC libraries were screened by hybridization (Koncz et al. (1992b), loc. cit.), using the ocs T-DNA-plant DNA junction fragment (BamHI-EcoRI fragment in FIG. 4A) as a probe. These clones were mapped and their fragments were subcloned and sequenced, in order to characterize the CPD cDNA (EMBL data base: accession number X87367; Seq ID No. 1) and gene (EMBL data base: accession number X87368; Seq ID No. 3). The 5'-end of the CPD transcript of 1735 bases was mapped 166 bp upstream of the ATG codon (data not shown), whereas the polyadenylation signal was located 104 nucleotides downstream of the stop codon in the 3'-UTR of 131 bases.

In support of the RNA hybridization data, nucleotide sequence comparison of the T-DNA insert junctions with wildtype cDNA and genomic DNA sequences showed that the T-DNA was inserted 10 bp 3'-downstream of the ATG start codon of a gene, preventing the transcription of its coding region.

DNA analyses and cloning, screening of lambda phage libraries, DNA and RNA filter hybridizations and sequencing of double-stranded DNA templates were performed using standard molecular techniques (Sambrook et al. (1989), loc. cit.). For hybridization of RNA blots, the following cDNA probes were used: RBCS (EST ATTS0402, GenBank (gb): X13611), CAB140 (Ohio Arabidopsis Stock Center (OASC) 38A1T7, gb A29280), alkaline peroxidase (EST ATTS0366, gb P24102), nonchloroplastic SOD (OASC 2G11T7P), GST2 (gb L11601), HSP70 (gb M23108), lignin-forming peroxidase (EST ATTS0592, gb P11965), chalcone synthase (Trezzini et al., Plant Mol. Biol. 21 (1993), 385–389), lipoxygenase (Lox2, gb L23968), S-adenosyl-methionine synthase (OASC 40G2T7, gb P23686), Hsp18.2 (gb X17295), ADH (gb M12196), PR1, PR2 and PR5 (Uknes et al., Plant Cell 4 (1992), 645–656).

The RNA blot shown in FIG. 4B was hybridized with plant DNA sequences flanking the hpt-pBR segment of the T-DNA (PstI-HindIII fragment in FIG. 4A).

EXAMPLE 4

Analysis Of The cpd cDNAs And Genomic Clones

The analysis of CPD DNAs and derived protein sequences was performed using the GCG and BLAST computer programs (Deveraux et al., Nucl. Acids Res. 12 (1984), 387–395; Altschul et al., J. Mol. Biol. 215 (1990), 403–410), as well as P450 sequence compilations (Gotoh, J. Biol. Chem. 267 (1992), 83–90; Nelson et al., DNA 12 (1993), 1–51; Frey et al., Mol. Gen. Genet. 246(1995), 100–109).

Figure 3B:
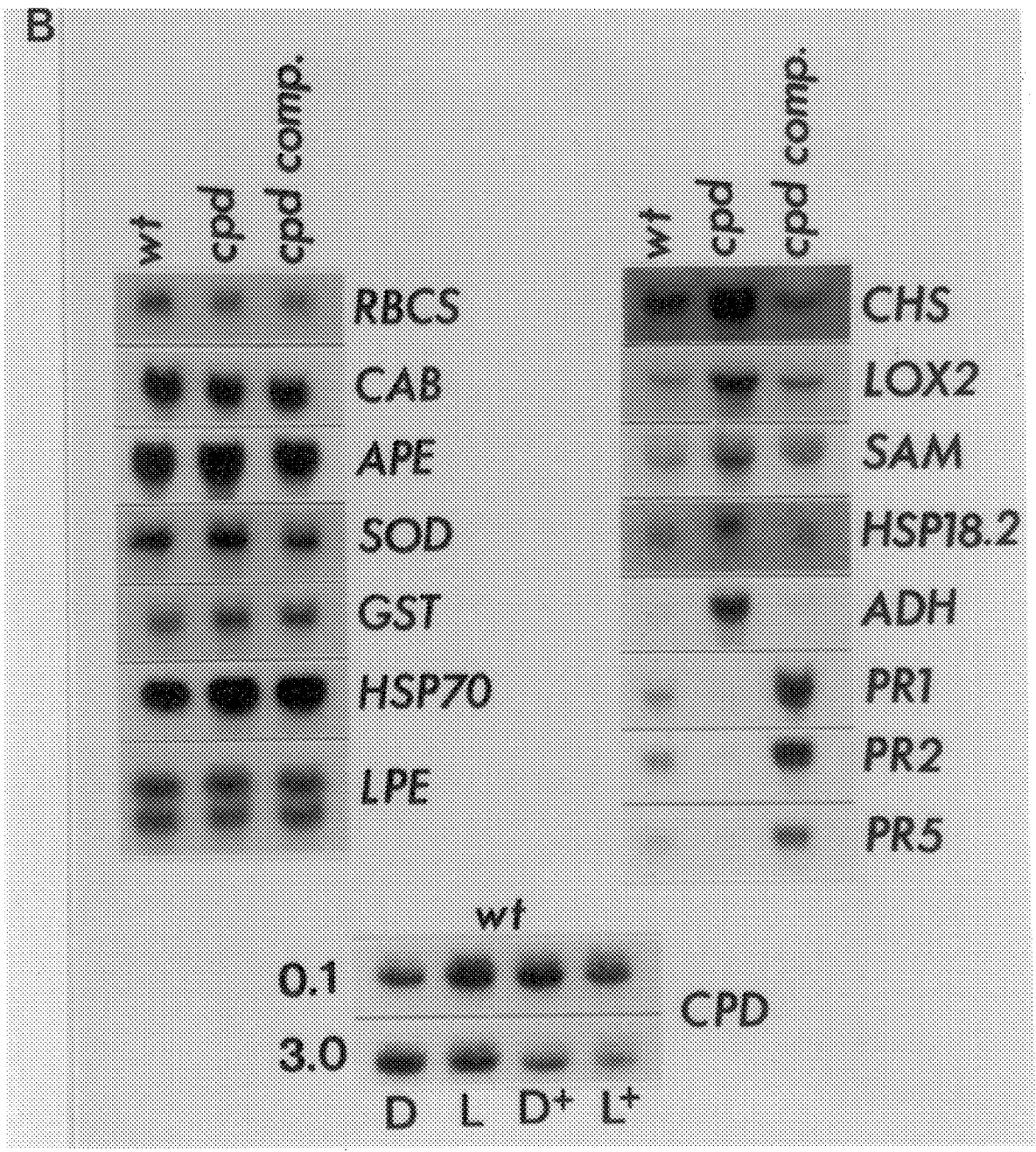

DNA sequence analysis revealed that the CPD gene (Seq ID No. 3) consists of 8 exons (FIG. 4A) with consensus splice sites at the exon-intron boundaries. The CPD cDNA (Seq ID No. 1) showed over 90% homology with expressed sequence tags [e.g. ESTs EMBL Z29017 and GenBank T43151] from several organ specific Arabidopsis cDNA libraries, indicating that the CPD transcript is ubiquitous. Hybridization analysis with the cDNA probe (FIG. 4B) indeed showed that the levels of steady-state CPD mRNA were comparable in roots, leaves and flowers, but considerably lower in inflorescence-stems and green siliques (fruits). The expression of the CPD gene was found to be modulated by external signals, such as light, cytokinin growth factor and sucrose provided as carbon source. The levels of CPD mRNA were elevated in dark-grown wild type seedlings by either increasing the sucrose content of the media (from 3 mM to 90 mM) or by light at low concentrations of sucrose, but decreased by combined cytokinin and sucrose treatments, particularly in the light (FIG. 3B).

Translation of the CPD cDNA defined a coding region of 472 codons (Seq ID No. 2) for a protein of 53,785 Da, in the following referred to as CYP90. The deduced amino acid sequence of this protein detected homology in the database with the conserved N-terminal membrane-anchoring, proline-rich, oxygen and heme binding domains of microsomal cytochrome P450s (FIG. 6); 50 to 90% sequence identity with conserved P450 domains defined by Nebert and Gonzalez (Ann. Rev. Biochem. 56 (1987), 945–993). The CPD gene encoded protein thus appeared to possess all functionally important domains of P450 monooxygenases (Pan et al., J. Biol. Chem. 270 (1995), 8487–8494). In addition, the sequence comparison also indicated a homology between CYP90 and specific domains of steroid hydroxylases. Members of the CYP2 family, including the rat testosterone-16a-hydroxylase (CYP2B1; 24% identity; Fujii-Kuriyama et al., Proc. Natl. Acad. Sci. 79 (1982), 2793–2797) showed thus sequence similarity with CYP90 in their central variable region (positions 135–249, FIG. 6), carrying the steroid substrate-binding domains SRS2 and SRS3 (Gotoh, (1992), loc. cit.). Moreover, in the CYP21 family, represented by the human progesterone-21-hydroxylase (CYP21A2; 19% identity; White et al., Proc. Natl. Acad. Sci. 83 (1986), 5111–5115), the positions of introns 7 and 8 corresponded to those of introns 3 and 5 in the CPD gene, suggesting a significant evolutionary relationship (Nelson et al., (1993), loc. cit.). Nonetheless, because its overall sequence identity with other P450s was less than 40%, the CPD gene product was assigned to a novel P450 family, CYP90, clustering on the evolutionary tree with CYP85 from tomato, CYP87 from sunflower (both unpublished) and CYP88 from maize (Winkler and Helentjaris, Plant Cell 7 (1995), 1307–1317; P450 Nomenclature Committee, D. Nelson, personal comm.).

EXAMPLE 5

Complementation Of The cpd Mutation

Figure 5B:
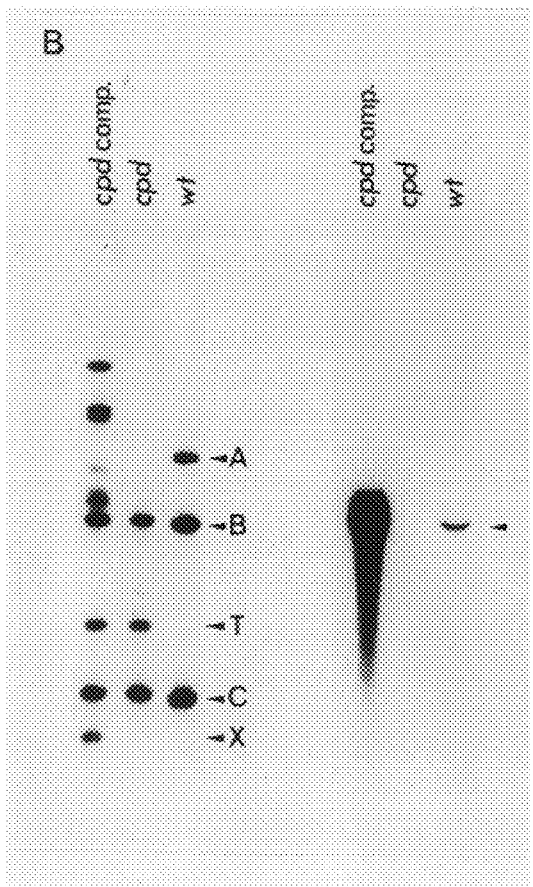
Figure 5C:
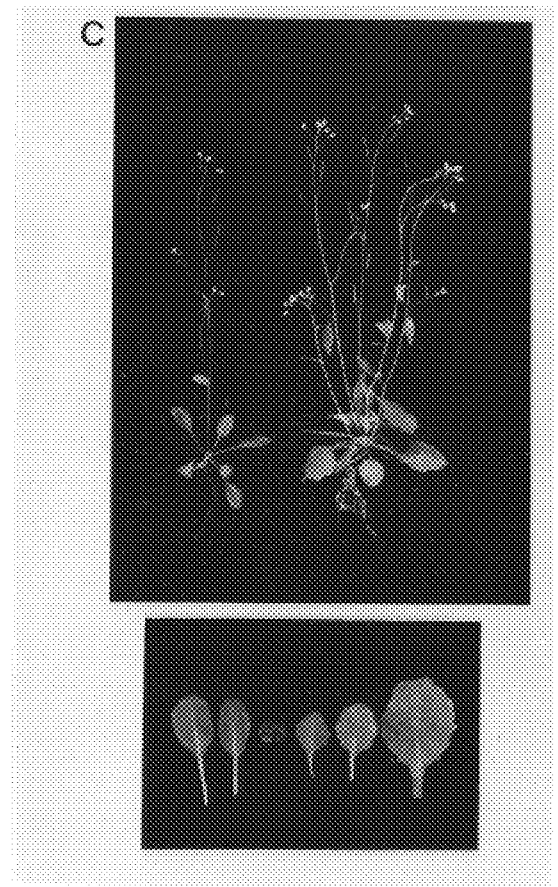

To demonstrate that the T-DNA insertion was indeed responsible for the cpd mutation, the coding region of the longest wildtype CPD cDNA (extending 47 bp ustream of the ATG codon) was cloned in the BamHI-site of plant gene expression vector pPCV701, conjugated from *E.coli* to Agrobacterium, and transformed into the homozygous cpd mutant by Agrobacterium-mediated Arabidopsis transformation as described (Koncz et al. (1994), loc. cit.). The cDNA was expressed in the homozygous cpd mutant under the control of the auxin-regulated mannopine synthase (mas) 2' promoter (FIG. 5A; Koncz et al. (1994), loc. cit.). Transgenic plants, selected and regenerated with the aid of a kanamycin resistance gene carried by the pPCV701 vector, were all wildtype and fertile, demonstrating genetic complementation of the cpd mutation. Kanamycin resistant progeny of many complemented lines developed more expanded leaves and inflorescence branches than the wild type. One such complemented cpd line (FIG. 5C) contained at least 3 independently segregating pPCV701 T-DNA insertions, since it yielded 268 kanamycin resistant wildtype and 4 kanamycin sensitive cpd mutant progeny. DNA fingerprinting confirmed the presence of multiple pPCV701 T-DNA insertions in this complemented line which produced a considerably higher amount of CPD transcript from the mas 2' promoter driven cDNA copies than the wild type from the single copy CPD gene (FIG. 5B).

EXAMPLE 6

Effects Of Overexpression Of A cpd cDNA

In contrast to the dark-grown cpd mutant (FIG. 3A), in light-grown plants neither the absence nor the overexpression of CPD transcript affected the level of steady-state RNAs of light-regulated RBCS and CAB genes (FIG. 3B). The transcript levels of chalcone synthase (CHS), alcohol dehydrogenase (ADH), lipoxygenase (LOX2), S-adenosyl-methionine synthase (SAM) and heat shock 18.2 (Hsp18.2) genes were elevated in the cpd mutant, whereas the mRNA levels of other stress-regulated genes, such as alkaline peroxidase (APE), superoxide dismutase (SOD), glutathione-S-transferase (GST), heat shock 70 (HSP70) or lignin forming peroxidase (LPE), were comparable in the cpd mutant, wildtype and CPD overexpressing plants. The expression of the pathogenenesis related genes PR1, 2 and 5 were remarkably low in the cpd mutant. However, overexpression of the CPD cDNA resulted in a significant induction of these PR genes in the complemented lines overexpressing cpd.

EXAMPLE 7

Complementation Of cpd Mutants With Brassinosteroids And Other Plant Growth Factors The above described sequence homology data were not sufficient to predict unambiguously the substrate specificity of CYP90 (Nelson et al. (1993), loc. cit.). Therefore, the elongation response of the cpd mutant to all plant growth factors, whose synthesis could involve P450 enzymes, was tested.

Plant growth factors including auxins (indole-3-acetic acid, a-naphthaleneacetic acid, 2,4-dichloro-phenoxyacetic acid), cytokinins (6-benzyl-aminopurine, 6-furfurylaminopurine, 6-(γ,γ-dimethylallylamino)-purine riboside), abscisic acid, salicylic acid, methyl-jasmonate, as well as retinoic acid derivatives (vitamin A aldehyde, 9-cis-retinal, 13-cis-retinal, trans-retionoic acid, 13-cis-retinoic acid and retinol) were used at final concentrations of 0.01, 0.05, 0.1, 0.5 or 1 $\mu$M, whereas gibberellins (gibberellic acid GA3, GA4, GA7 and GA13) were applied at 0.1, 1, 10, and 100 $\mu$M concentrations in MSAR seed germination media.

Brassinosteroids as listed in FIG. 1 and epi-isomers of teasterone, typhasterol, castasterone and brassinolide were obtained from A. Sakurai and S. Fujioka (Institute of Physical and Chemical Research (RIKEN), Japan) and G. Adam (Institute for Plant Biochemistry, Halle, Germany). BRs were tested at similar concentrations (0.005, 0.01, 0.05, 0.1, 0.5 and 1 $\mu$M) in MSAR media used for seed germination under aseptic conditions (Koncz et al. (1994), loc. cit. ). The bioassays were evaluated after 1, 2, 5 and 10 days of germination by measurement of the length of hypocotyls and roots, as well as by visual inspection and photography of seedlings. Mutant plants grown in soil were sprayed with 0.1 or 1 $\mu$M aqueous solutions of castasterone or brassinolide.

Histological analyses were performed according to standard procedures (Feder and O'Brien, Am. J. Bot. 55 (1968), 123–142). Tissues were fixed in formalin:acetic acid:ethanol (90:5:5), embedded in 2-hydroxyethyl methacrylate, sectioned at 10 $\mu$m using a rotary microtome, and stained by toluidine-blue. To prepare contact imprints, seedlings were placed in 3% molten agarose and carefully removed from the solidified carrier before taking pictures.

In these bioassays auxins, gibberellins, cytokinins, abscisic acid, ethylene, methyl-jasmonate, salicylic acid and different retinoid acid derivatives failed to promote the hypocotyl elongation of the cpd mutant grown in the dark or light (data not shown). However, brassinolide, an ecdysone-like plant steroid (used at concentrations of 0.005 to $1 \times 10^{-6}$M), was found to restore cell elongation in the hypocotyl, leaves and petioles of cpd mutant seedlings in both dark and light. Brassinolide treatment also restored the male fertility of the mutant, allowing the production of homozygous seeds.

When grown in the presence of C23-hydroxylated brassinosteroid (BR) precursors (0.1 to $1 \times 10^{-6}$M) of brassinolide, such as teasterone, 3-dehydroteasterone, typhasterol, and castasterone (Fujioka et al., Biosci. Biotech. Biochem. 59 (1995), 1543–1547), the cpd mutant was also indistunguisable from wild type in both dark and light (FIG. 7). However, cathasterone and its precursor campesterol (as well as campestanol, 6α-hydroxycampestanol and 6-oxocampestanol, $\Delta^{22}$-6-oxocampestanol and 22α,23α-epoxy6-oxocampestanol, data not shown), which do not carry hydroxyl moiety at the C23 position, did not alter the cpd phenotype, suggesting a deficiency of cathasterone C23-hydroxylation to teasterone in the cpd mutant. From the synthetic [22R,23R,24R]-derivatives of BRs (Adam and Marquardt, (1986), loc. cit.) epi-teasterone was found to be inactive, whereas epi-castasterone and epi-brassinolide rescued the cpd phenotype as well as their [22R,23R,24S]-stereoisomers.

Remarkably, the hypocotyl elongation response of wild-type seedlings was unaffected by brassinosteroids in the dark (FIG. 7), indicating a possible saturation of this growth response. In contrast, treatments of wildtype seedlings with castasterone and brassinolide in the light promoted hypocotyl elongation (albeit with different efficiencies). When applied at higher concentrations (0.1 to $1 \times 10^{-6}$M), castasterone and brassinolide (as well as their epi-stereoisomers, but not other BRs precursors) caused aberrant leaf expansion, epinasty, senescence and retarded development in both wild type and mutant plants grown in the light (FIG. 7).

EXAMPLE 8

Identification Of Other Mutants Affected In Brassinosteroid Responses

Physiological data indicate that the biosynthesis of gibberellins and steroids involve common precursors (Davies, Plant hormones and their role in plant growth and development (1987), Dordrecht, The netherlands: Martinus Nijhoff Publ.) and that BRs stimulate ethylene biosynthesis in the light (Mandava (1988), loc. cit.). Nonetheless, mutants affected in ethylene production (eto1), gibberellin biosynthesis (ga) and perception (gai) do not respond to BRs in the dark, and BRs promote only a weak hypocotyl elongation response in the ethylene resistant etr1 mutant. Thus, mutants affected in ethylene, gibberellin and BR responses can clearly be distinguished. The BR-bioassays performed with cpd mutant and wild type Arabidopsis seedlings in the dark show that BR-deficiency can result in a short hypocotyl phenotype, although BRs do not stimulate hypocotyl elongation in the wildtype. Mutants deficient in BR biosynthesis are expected therefore to develop short hypocotyls, which should be restored to wildtype by brassinolide and BR precursors. One can also predict that mutants defective in BR-perception and/or signaling will show short hypocotyl and a partial or complete insensitivity to BRs. The de-etiolated mutant det2 appears to be a BR biosynthetic mutant. The DET2 gene codes for a homolog of animal steroid-5a-reductases which is probably required for the conversion of campesterol to campestanol in the first step of brassinolide biosynthesis (Li, J., P. Nagpal, V. Vitart and J. Chory, personal com.). In other de-etiolated and constitutive photomorphogenic mutants, such as det1, cop1-16, fus4, fus5, fus6, fus7, fus8, fus9, fus11, and fus12, BRs stimulate hypocotyl elongation only in the dark. The cop1-13 mutant, which produces no COP1 protein (McNellis et al., Plant Cell 6 (1994), 487–500), is apparently insensitive to BRs. In contrast, the less severe cop1-16 mutant (Miséra et al., Mol. Gen. Genet. 244 (1994), 242–252; McNellis et al. (1994) loc. cit.), synthesizing an immunologically detectable amount of mutant COP1 protein, responds to BRs by hypocotyl growth. The fus6 mutant displays similar allelic differences, whereas the det3 mutant shows a complete insentivity to BRs. It is therefore possible that these mutations affect regulatory functions involved in BR perception and/or signaling.

The effect of castasterone and brassinolide (and their epi-isomers) on different Arabidopsis mutants impaired in hypocotyl elongation was similarly tested. To avoid complexity resulting from negative regulation of the hypocotyl elongation by light, the mutants were germinated in the presense or absence of BRs in the dark and their hypocotyl growth was compared to that of untreated and ergosterol-treated seedlings as controls (FIG. 8). Mutants in gibberellin biosynthesis (ga5) or perception (gai), showing dwarfism and inhibition of hypocotyl and/or epicotyl growth in the light (Finkelstein and Zeevaart, in Arabidopsis (1994), Meyerowitz and Sommerville (Eds.) Cold spring Harbor Laboratory Press; Cold spring Harbor, N.Y., 523–553), developed similar or shorter hypocotyls as the wild type, but did not respond to BRs by significant hypocotyl elongation (more than 20%) in the dark. The inhibition of hypocotyl growth in the dark-grown ethylene overproducing mutant eto1 (Ecker, Science. 268 (1995), 667–675) was also unaffected by BRs. In contrast, BR-treatments stimulated the rate of hypocotyl elongation by 50 to 80% in the ethylene resistant mutant etr1 (Ecker (1995), loc. cit.). The hypocotyl elongation of the auxin/ethylene resistant axr2 mutant (Estelle and Klee, in Arabidopsis (1994), Meyerowitz and Sommerville (Eds.) Cold spring Harbor Laboratory Press; Cold spring Harbor, N.Y., 555–578) was also increased 2 to 3-fold by BRs, which promoted the enlargement of cotyledons, but inhibited the root growth of axr2 seedlings. The wild type and the ga5, gai1, eto1, etr1, and axr2 mutants displayed comparable hypocotyl elongation (but different epicotyl/stem growth) responses to BRs in the light.

As was observed for the cpd mutant, castasterone and brassinolide restored the phenotype of the dim mutant (Takahashi et al., Genes Dev. 9 (1995), 97–107) to wild type in the dark, as well as in the light (data not shown). In contrast, the hypocotyl elongation of det1, cop1-16, fus4, fus5, fus6, fus7, fus8, fus9, fus11, and fus12 mutants (Chory and Susek, in : Arabidopsis (1994), Meyerowitz and Sommerville (Eds.) Cold spring Harbor Laboratory Press; Cold spring Harbor, N.Y., 579–614; Deng, Cell 76 (1994), 423–426; Miséra et al. (1994), loc. cit.) was stimulated 3 to 10 -fold by BRs only in the dark. BRs inhibited the elongation of roots in these mutants. BRs also stimulated the cell enlargement and decreased the accumulation of anthocyanins in the cotyledons of det1 and fus9 mutants. In comparison to their allelles, the cop1-13 and fus6-G mutants showed no, or respectively a minimal (10 to 20%), hypocotyl elongation response to castasterone and brassinolide, whereas the det3 mutant (Chory and Susek (1994), loc. cit.) was found to be completely insensitive to Brs.

The data presented by the present application clearly provide evidence that brassinosteroids are of crucial importance for plant growth and development. Since their discovery (Grove et al., Nature 281 (1979), 216–217), brassinosteroids (BRs) have been considered to be nonessential plant hormones, because their concentration is extremely low in most plant species and their action spectrum is redundant with those of ubiquitous growth factors auxin, gibberellin, ethylene and cytokinin. A major argument supporting this view is that BRs are inactive in hypocotyl elongation assays performed in the dark, which are used as standard tests to monitor the activity of photoreceptors and phytohormones controlling cell elongation (for review see Davies (1987), loc. cit.; Kendrick and Kronenberg, Photomorphogenesis in plants; Dordrecht, The Netherlands: Kluwer Academic Publ. (1994)). The data described in the present application clearly undermine this argument, since they demonstrate that the phenotype of a hypocotyl elongation mutant can be restored to wild type by brassinolide and its precursors, but not by other known plant growth factors. The BR-precursor feeding experiments suggest that the hypocotyl elongation defect in the cpd mutant results from a deficiency in brassinolide biosynthesis. Brassinolide has been observed in many plant species to stimulate the longitudinal arrangement of cortical microtubuli and cellulose microfilaments, leaf unrolling, xylem differentiation and hypocotyl elongation in the light. Brassinolide is also reported to inhibit root elongation, radial growth of the stem, anthocyanin synthesis, and de-etiolation (Mandava (1988), loc. cit.). Phenotypic traits of the cpd mutant—such as the inhibition of longitudinal cell elongation in most organs, the transverse arrangement of cellulose microfilaments on the surface of epidermal cells, the inhibition of leaf unrolling and xylem differentiation, and the induction of de-etiolation in the dark—are consistent with a phenotype expected for a mutant in brassinolide synthesis. In addition, the conservation of exon-intron boundaries between the CPD gene and CYP21 gene family of progesterone side-chain hydroxylases, the homology of the CYP90 protein with all conserved domains of functional P450 monooxygenases, and the similarity of CYP90 domains with the substrate binding regions of CYP2 testosterone hydroxylases also suggest that the CPD gene may code for a cytochrome P450 steroid hydroxylase.

Cytochrome P450s are known to use a wide range of artificial substrates in vitro, but perform well-defined stereospecific reactions in vivo. Because their substrate specificity can be altered by mutations affecting the substrate binding domains, the specificity of P450 enzymes can only be determined by in vivo feeding experiments with labeled substrates (Nebert and Gonzalez (1987), loc. cit.). Because it usually cannot be excluded that multiple cytochrome P450s contribute to a given metabolic conversion in vivo, such an analysis requires either the overexpression of cytochrome P450s in transgenic organisms, or mutants deficient in particular P450s. The cpd mutant and CPD overexpressing transgenic plants therefore provide a suitable material to confirm the requirement of CYP90 for C23-hydroxylation of cathasterone in brassinolide biosynthesis (Fujioka et al. (1995), loc. cit.).

The cpd and det2 mutations result in similar phenotypic traits, including the induction of de-etiolation and expression of light-induced RBCS and CAB genes in the dark. Thus, cpd can be considered to be a new type of det mutation. Genetic analyses of detlhy double mutants suggest that det1 and det2 are epistatic to the hy mutations of photoreceptors. Therefore, det1 and det2 have been proposed to act in parallel light signaling pathways as negative regulators of de-etiolation (Chory and Susek (1994), loc. cit.). In the det1 pathway, the products of DET1, COP1, and some FUS genes are thought to function as nuclear repressors of light-regulated genes in the dark (Deng (1994), loc. cit.); Quail et al., Science 268 (1995), 675–680). Now, the putative det2 light signaling pathway (Chory and Susek (1994), loc. cit.) appears to be a brassinosteroid pathway, because det2 as well as cpd and dim mutants are restored to wild type by BRs. This is consistent with data indicating that BRs inhibit de-etiolation in the dark (Mandava (1988), loc. cit.). Our data also show that the cpd mutation results in the activation of stress-regulated chalcone synthase (CHS), alcohol dehydrogenase, heat shock 18.2, lipoxygenase, S-adenosyl-methionine synthase genes in the light. This correlates with the observations showing that BRs suppress anthocyanin synthesis (i.e. controlled by CHS; Mandava (1988), loc. cit.) and that the CHS gene is also induced in the det2 mutant (Chory et al., Plant Cell 3 (1991), 445–459). The CPD function (and thus the det2/BR-pathway) appears therefore to negatively regulate stress signaling, possibly via the modulation of lipoxygenase involved in the generation of lipid hydroperoxide signals (i.e jasmonate), which are known to control defense and stress responses in plants (Farmer, Plant Mol. Biol. 26 (1994), 1423–1437). Cytokinin treatment of wild type Arabidopsis has been observed to result in a phenocopy of the det2 mutation (Chory et al., Plant Physiol. 104 (1994), 339–347). In agreement, our data show that the transcription of the CPD gene is downregulated by cytokinin, which may thus control BR-biosynthesis. The expression of the CPD gene is also modulated by light and the availability of carbon source (e.g. sucrose), suggesting complex regulatory interactions between light and BR signaling. It is therefore possible that the cpd and det2 mutations only indirectly affect the expression of light-regulated genes (e.g. through the regulation of stress responses). Studies of the dim mutant indicate that inhibition of the hypocotyl elongation may not influence the expression of light-induced RBCS, CAB and CHS genes in the dark (Takahashi et al. (1995), loc. cit.). This is intriguing, because the phenotypic traits of the dim mutant are nearly identical with those of the cpd and det2 mutants, and our precursor feeding experiments suggest that dim causes a deficiency before typhasterol in BR-biosynthesis (unpublished). A comparative analysis of det2, cpd, and dim mutants, including their combinations with hy loci, is therefore necessary to clarify how the regulation of light-induced genes is affected by brassinolide and/or its brassinosteroid precursors. Unlike det2, the dim mutation has been proposed to control cell elongation by specific regulation of the tubulin TUB1 gene expression (Takahashi et al. (1995), loc. cit.). In fact, the available genetic data do not prove that the signaling pathways identified by the det1 and det2 mutations are exclusively involved in light signaling (Millar et al., Ann. Rev. Genet. 28 (1994), 325–349). Therefore, DET, COP, FUS, and CPD genes can also be considered to act as positive regulators of cell elongation, because their mutations result in the inhibition of hypocotyl elongation in the dark. The fact, that BRs can compensate the cell elongation defects caused by the det1, cop1 and fus mutations suggests a close interaction between the det1 and det2 pathways, as proposed by the genetic model (Chory and Susek (1994), loc. cit.). BR-insensitivity of the cop1-13 mutant may in fact point to a possible involvement of the COP1 WD-protein (Deng et al., Cell 71 (1992), 791–801) in BR-responses.

We claim:

1. An isolated nucleic acid molecule encoding a protein having the enzymatic activity of a cytochrome P450-type hydroxylase or encoding a biologically active fragment of such a protein, selected from the group consisting of:
 (a) nucleic acid molecules coding for a polypeptide having the amino acid sequence given in SEQ ID NO: 2;
 (b) nucleic acid molecules comprising the coding region of the nucleotide sequence given in SEQ ID NO: 1;
 (c) the nucleic acid molecule of SEQ ID NO: 3;
 (d) nucleic acid molecules hybridizing under stringent conditions to a nucleic acid molecule of (a), (b) or (c); and
 (e) nucleic acid molecules which are degenerate to the nucleic acid molecules of any one of (a) to (d).

2. The nucleic acid molecule according to claim 1, wherein the encoded protein is a hydroxylase which is involved in the conversion of cathasterone to teasterone.

3. The nucleic acid molecule according to claim 1 or 2 which is DNA.

4. A nucleic acid probe specifically hybridizing with a nucleic acid molecule according to claim 3.

5. A vector comprising a nucleic acid molecule according to claim 3.

6. The vector according to claim 5 in which the nucleic acid molecule is linked to regulatory elements which allow for the expression of the nucleic acid molecule in procaryotic or eucaryotic cells.

7. A host cell which is transformed in a stable manner with a vector according to claim 5.

8. The host cell according to claim 7 which is a bacterial, fungal, plant or animal cell.

9. A process for the preparation of a protein encoded by a nucleic acid molecule encoding a protein having the enzymatic activity of a cytochrome P450-type hydroxylase or encoding a biologically active fragment of such a protein, selected from the group consisting of:
 (a) nucleic acid molecules coding for a polypeptide having the amino acid sequence given in SEQ ID NO: 2;
 (b) nucleic acid molecules comprising the coding region of the nucleotide sequence given in SEQ ID NO: 1;
 (c) the nucleic acid molecule of SEQ ID NO: 3;
 (d) nucleic acid molecules hybridizing under stringent conditions to a nucleic acid molecule of (a), (b) or (c); and
 (e) nucleic acid molecules which are degenerate to the nucleic acid molecules of any one of (a) to (d),
or a biologically active fragment thereof, comprising:
 (1) cultivating a host cell according to claim 7 under conditions allowing expression of the nucleic acid sequence; and
 (2) recovering the resulting protein from the cell culture.

10. A transgenic plant cell, comprising:
 a nucleic acid molecule according to claim 1 which is integrated in a stable manner into the genome of said plant cell, wherein said nucleic acid molecule is linked to regulatory elements allowing for the expression of said nucleic acid molecule in plant cells.

11. A transgenic plant, comprising transgenic plant cells according to claim 10.

12. The transgenic plant according to claim 11, in which brassinosteroid synthesis is altered.

13. A transgenic plant cell, comprising:
 a nucleic acid molecule selected from the group consisting of;
  (a) nucleic acid molecules coding for a polypeptide having the amino acid sequence given in SEQ ID NO: 2;
  nucleic acid molecules comprising the coding region of the nucleotide sequence given in SEQ ID NO: 1;
  (c) the nucleic acid molecule of SEQ ID NO: 3;
  (d) nucleic acid molecules hybridizing under stringent conditions to a nucleic acid molecule of (a), (b) or (c); and
  (e) nucleic acid molecules which are degenerate to the nucleic acid molecules of any one of (a) to (d),
 which has been integrated in a stable manner into the genome of said plant cell, wherein the expression of the nucleic acid molecule leads to a reduction in the synthesis in the cells of the polypeptide having the amino acid sequence given in SEQ ID NO: 2.

14. The transgenic plant cell according to claim 13, wherein the reduction is achieved by an antisense.

15. A transgenic plant comprising transgenic plant cells according to claim 13 or 14.

16. The transgenic plant according to claim 15, wherein said transgenic plant displays a deficiency in brassinosteroid synthesis.

17. The transgenic plant according to claim 15, wherein said transgenic plant displays at least one of the following features:
 dwarfism;
 reduced elongation of the hypocotyl of seed germinating in the dark;
 improved stress tolerance; and
 male sterility.

18. A cultured plant tissue comprising transgenic plant cells according to claim 10 or 13.

19. Harvestable parts of transgenic plants according to claim 11.

20. Harvestable parts of transgenic plants according to claim 16.

21. Propagation material of transgenic plants according to claim 11.

22. Propagation material of transgenic plants according to claim 15.

* * * * *